US011313846B1

(12) United States Patent
Haslbeck et al.

(10) Patent No.: US 11,313,846 B1
(45) Date of Patent: Apr. 26, 2022

(54) UNDERWATER SHIP HULL CLEANING TOOL TEST DEVICE

(71) Applicant: The United States of America, as represented by the Secretary of the Navy, Arlington, VA (US)

(72) Inventors: Elizabeth G. Haslbeck, Derwood, MD (US); Eric R. Holm, McLean, VA (US); Kody L. Lieberman, Arlington, VA (US); Patrick J. Earley, San Diego, CA (US); Ignacio D. Rivera, San Diego, CA (US); Derek M. Michelin, Plymouth, MA (US); Nathan H. Gabriel, Powell, OH (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 17/169,441

(22) Filed: Feb. 6, 2021

Related U.S. Application Data

(60) Provisional application No. 62/972,436, filed on Feb. 10, 2020.

(51) Int. Cl.
*B63B 59/00* (2006.01)
*B08B 1/00* (2006.01)
(Continued)

(52) U.S. Cl.
CPC .............. *G01N 33/18* (2013.01); *B08B 1/02* (2013.01); *B63B 59/00* (2013.01); *G01L 5/00* (2013.01); *G01P 3/00* (2013.01)

(58) Field of Classification Search
CPC ......... B63B 59/08; B63B 59/10; B63B 59/06; B63B 59/04; B63B 71/00;
(Continued)

(56) References Cited

U.S. PATENT DOCUMENTS

| 3,906,572 | A | | 9/1975 | Winn | |
| 3,946,692 | A | * | 3/1976 | Sierra | ..................... B63B 59/10 |
| | | | | | 114/222 |

(Continued)

FOREIGN PATENT DOCUMENTS

| CN | 214262495 U | * | 9/2021 |
| SU | 1574505 A | * | 6/1990 |
| SU | 1615048 A | * | 12/1990 |

OTHER PUBLICATIONS

Elizabeth Haslbeck, "Impact of Cleaning Tools on Wear of Biofouling Control Coating Systems and Copper and Zinc Release," WP-2018-5194, SERPD-ESTCP In-Progress Review Meeting, Feb. 13, 2019, 32-page slide presentation.

(Continued)

*Primary Examiner* — Andre J Allen
(74) *Attorney, Agent, or Firm* — Howard Kaiser

(57) ABSTRACT

Exemplary inventive practice replicatively tests the effects of cleaning processes applied to marine hulls coated with biofouling-control substances. A sample (e.g., antifouling-coated panel) is coupled with a trolley that is linearly moveable via trolley wheels upon two parallel tracks provided along the length of an open rectangular box-shaped tank, partially filled with natural or artificial seawater. The cleaning element (e.g., brush bristles) points vertically upward in a stationary position atop a motorized cleaning unit installed proximate the bottom of the tank. In accordance with the trolley's horizontal movement, and while the sample and cleaning element are immersed in seawater, the sample traverses the cleaning element in a contactual manner that mimics underwater cleaning dynamics for a hull surface. Using sensory data, seawater portions are evaluated to relate the cleaning instrumentation and operation to the (Continued)

nature and degree of biocides and chemicals that, concomitant the cleaning, are released into the seawater.

17 Claims, 15 Drawing Sheets

(51) Int. Cl.
    *G01N 33/18*     (2006.01)
    *B08B 1/02*     (2006.01)
    *G01L 5/00*     (2006.01)
    *G01P 3/00*     (2006.01)

(58) Field of Classification Search
    CPC ........ B63B 2059/087; B63B 2059/082; B63B 17/00; B63B 1/36; B63B 2231/30; B63B 57/00; B63B 59/00; B63B 59/045; B63B 2059/085; B63B 21/00; B63B 25/006; B63B 57/02; B63B 59/02
    USPC .......................................................... 114/222
    See application file for complete search history.

(56) References Cited

U.S. PATENT DOCUMENTS

| | | | |
|---|---|---|---|
| 4,011,827 A | | 3/1977 | Fond |
| 4,060,047 A | * | 11/1977 | Sabella ............... B63B 59/08 114/222 |
| 4,236,477 A | * | 12/1980 | Norris ................. B63B 59/08 114/222 |
| 4,462,328 A | * | 7/1984 | Oram ................... B63B 59/10 114/222 |
| 4,574,722 A | | 3/1986 | Orita et al. |
| 4,648,344 A | * | 3/1987 | Burgers ............... B63B 59/08 114/222 |
| 4,841,894 A | * | 6/1989 | Nellessen, Jr. ...... B63B 59/08 114/222 |
| 4,991,533 A | * | 2/1991 | Sterling .............. B63B 59/08 114/222 |
| 5,174,222 A | * | 12/1992 | Rogers ................ B63B 59/08 114/222 |
| 5,222,452 A | | 6/1993 | Maloney |
| 5,849,099 A | * | 12/1998 | McGuire .............. B44D 3/16 134/10 |
| 5,947,051 A | | 9/1999 | Geiger |
| 6,070,547 A | | 6/2000 | Achord |
| 7,437,959 B1 | | 10/2008 | Chadwick et al. |
| 7,444,891 B1 | | 11/2008 | Chadwick et al. |
| 7,971,547 B1 | | 7/2011 | Hertel, III et al. |
| 8,506,719 B2 | | 8/2013 | Holappa et al. |
| 2005/0199171 A1 | * | 9/2005 | Ecklund ............... B63B 59/08 114/222 |
| 2007/0051291 A1 | * | 3/2007 | Hudd .................. B63B 59/08 114/222 |
| 2007/0079743 A1 | * | 4/2007 | Hudd .................. B63B 59/08 114/222 |
| 2021/0107607 A1 | * | 4/2021 | Gan .................... B08B 13/00 |

OTHER PUBLICATIONS

Patrick Earley and Elizabeth Haslbeck, "Impact of Cleaning Tools on Antifouling Coatings," SERPD-ESTCP Symposium 2019, Enhancing DoD's Mission Effectiveness, Dec. 3-5, 2019, Washington, DC, 14-page slide presentation.
Patrick Earley, Elizabelth Haslbeck, Eric Holm, Kody Lieberman, and Ignacio Rivera-Duarte, "Impact of Cleaning Tools on Antifouling Coatings," SERDP WP-1659-18 and ESTCP WP-2018-5194, SERPD-ESTCP Symposium 2019, Enhancing DoD's Mission Effectiveness, Dec. 3-5, 2019, Washington, DC, 1-page summary sheet.
Elizabeth Haslbeck, "Impact of Cleaning Tools on Antifouling Coatings," SERDP & ESTCP Webinar Series (#102), "Developing and Demonstrating Non-Toxic and Sustainable Coating Systems for Military Platforms," Oct. 31, 2019, 29-page slide presentation.
United States U.S. Appl. No. 62/972,436, filed Feb. 10, 2020, entitled "Underwater Ship Hui Cleaning Tool Test Device," inventors Elizabeth G Haslbeck et al., Navy Case No. 112,152.
John R. Myers, Arthur Horinek, and Matthew Rubai, "Automated Hull Maintenance Vehicle (AHMV) Brush Design and Characterization," Final Report, Contract No. N00167-96-C-0059, Jan. 1999, prepared for the United States Government by Battelle, Columbus, Ohio, 153 pages; see, esp., pp. 4-7 ("Brush Testing").
Dinis Reis Oliveira and Lena Granhag,"Ship Hull In-Water Cleaning and Its Effects on Fouling-Control Coatings," Biofouling (The Journal of Bioadhesion and Biofilm Research), 2020, vol. 36, No. 3, pp. 332-350, published online May 13, 2020.
Eric R. Holm, Elizabeth G. Haslbeck, and Arthur A. Horinek, "Evaluation of Brushes for Removal of Fouling from Fouling-release Surfaces, Using a Hydraulic Cleaning Device," Biofouling, Oct. 2003, vol. 19, No. 5, pp. 297-305.
Elizabeth Haslbeck, Eric Holm, and Kody Lieberman, "Challenges and Progress in Meeting a US Navy Fleet Need: Effective Underwater Hull Coatings for Biofouling Control," The 19th International Congress on Marine Corrosion and Fouling(ICMCF), Jun. 24-29, 2018, Florida Institute ofTechnology (FIT), Melbourne, Florida, 24-page slide presentation.
Kody Lieberman, Elizabeth Haslbeck, Eric Holm, Patrick Earley, and Ignacio Rivera, "Impact of Cleaning Tools on Wear of Biofouling Control Coating Systems and Copper and Zinc Release," WP-2018-5194, SERPD-ESTCP Symposium 2020, virtual event Nov. 30-Dec. 4, 2020, 9-page slide presentation.
Kody Lieberman, Elizabeth Haslbeck, Eric Holm, Patrick Earley, and Ignacio Rivera, "Impact of Cleaning Tools on Wear of Biofouling Control Coating Systems and Copper and Zinc Release," WP-2018-5194, SERPD-ESTCP Symposium 2021, virtual event Nov. 29-Dec. 3, 2021, 10-page slide presentation.
Elizabeth Haslbeck (Principal Investigator), "Cleaning Tool Test Device Io Support Quantifying the Impact of Cleaning fools on Wear of Biofouling Control Coating Systems and Copper and Zinc Release," WP18-1659, SERDP/ESTCP website, webpage (n.d.) https://www.serdp-estcp.org/Program-Areas/Weapons-Systems-and-Platforms/Noise-and-Emissions/WP18-1659/WP18-1659, 2 pages printed out on Jan. 13, 2022.
Elizabeth Haslbeck (Principal Investigator), "Impact of Cleaning Tools on Wear of Biofouling Control Coating Systems and Copper and Zinc Release," WP18-5194, SERDP/ESTCP website, webpage (n.d.) https://www.serdp-estcp.org/Program-Areas/Weapons-Systems-and-Platforms/WP18-5194/WP18-5194/(language)/eng-US, 2 pages printed out on Jan. 13, 2022.
Weapons Systems and Platforms, Active Projects, SERDP/ESTCP website, webpage (n.d.) https://www.sertip-estcp.org/index.php// Program-Areas/Weapons-Systems-and-Platfoims/(offset)/80/(list)/1/ (sort_order)/inv/(sort_by)/date/view_all)/1/, latest project start date indicated is Jan. 2022, 27 p. printed out on Jan. 13, 2022; see, esp., Project ID WP18-5194 (p. 12) and Project ID WP18-1659 (p. 13).

* cited by examiner

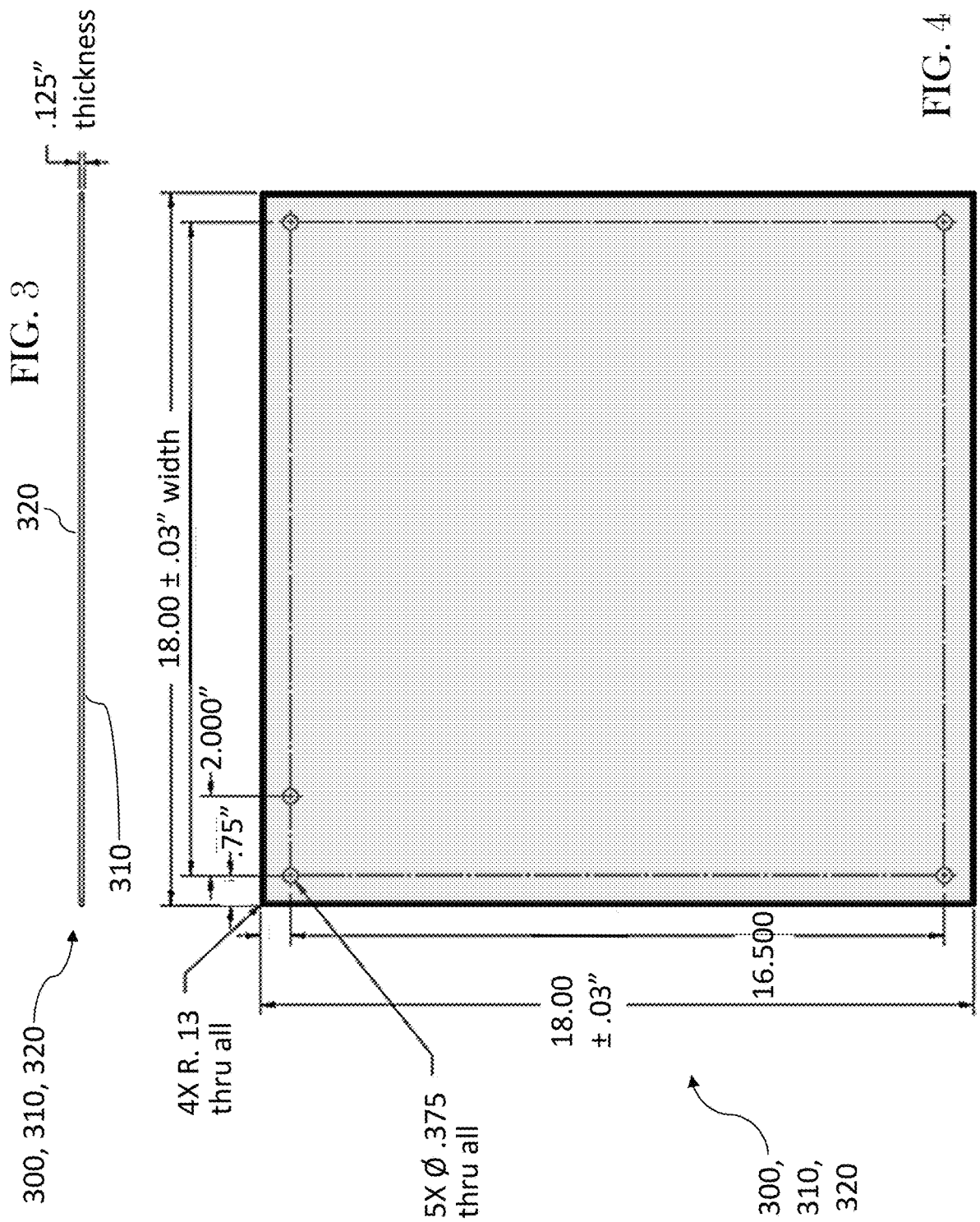

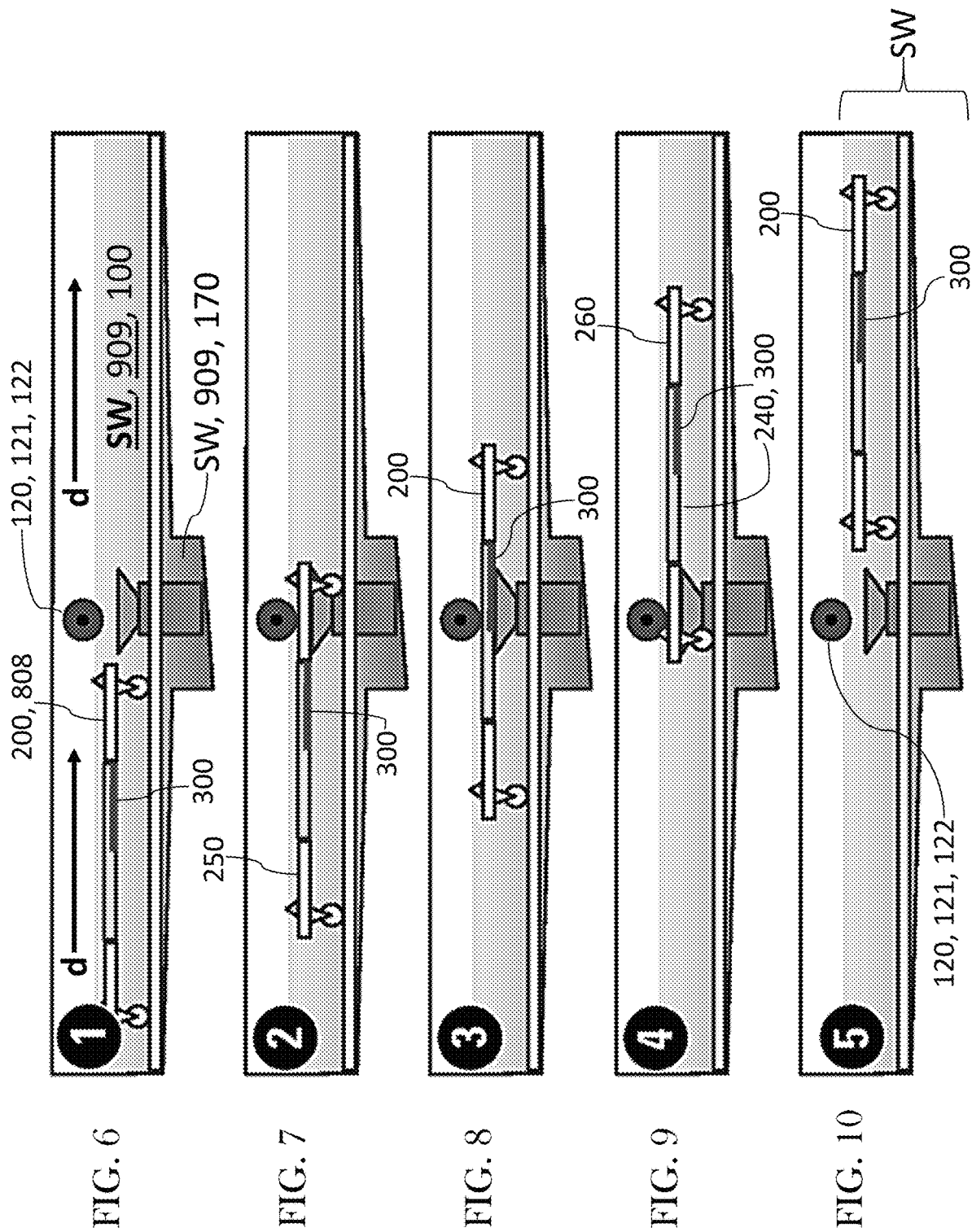

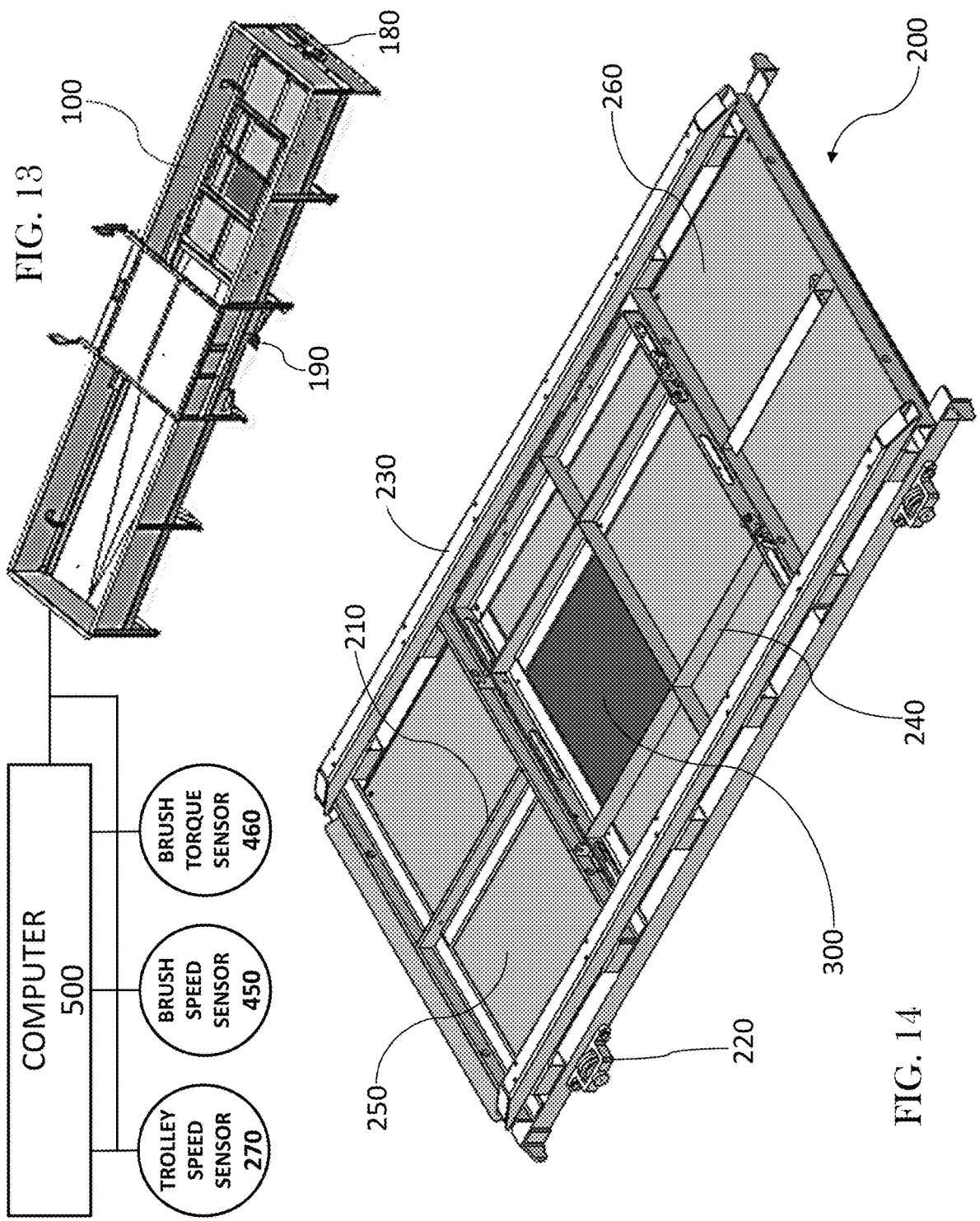

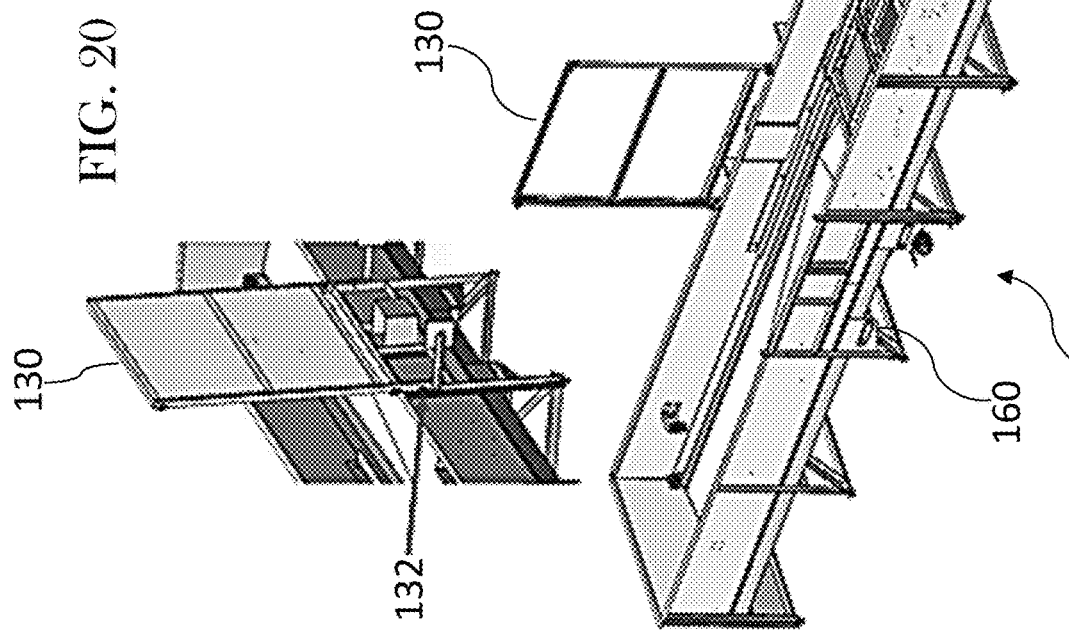
FIG. 20
FIG. 22
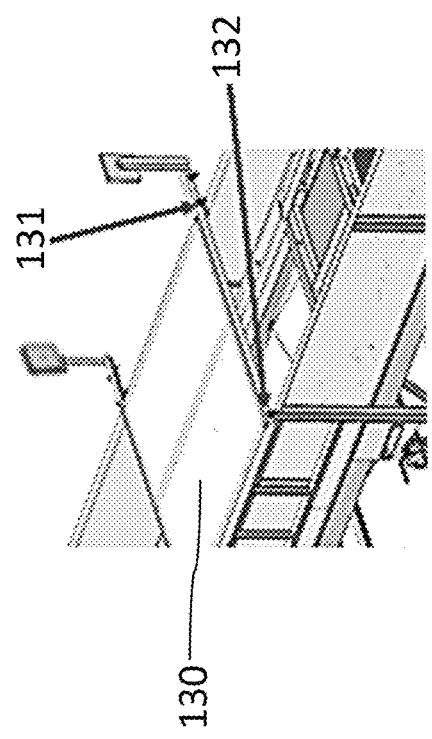
FIG. 19
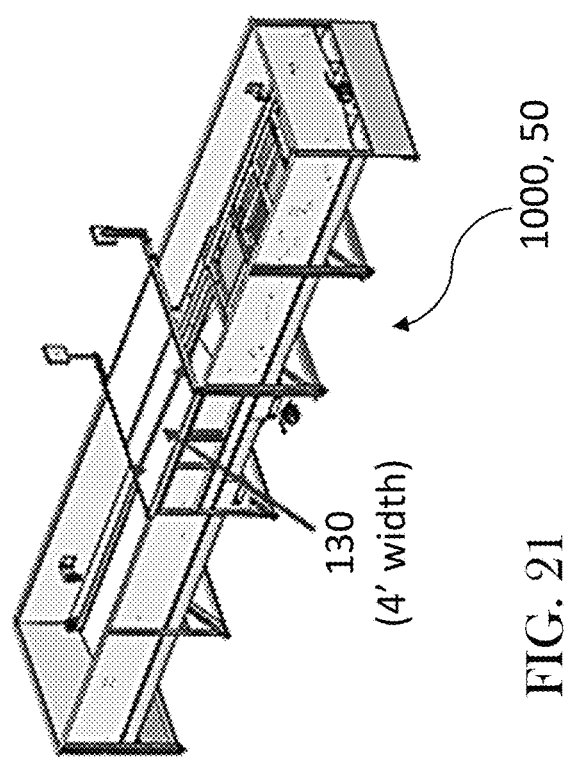
FIG. 21

UNDERWATER SHIP HULL CLEANING TOOL TEST DEVICE

CROSS-REFERENCE TO RELATED APPLICATIONS

This patent application claims the benefit of U.S. provisional patent application No. 62/972,436, filed 10 Feb. 2020, hereby incorporated herein by reference, entitled "Underwater Ship Hull Cleaning Tool Test Device," inventors Elizabeth G. Haslbeck et al.

STATEMENT OF GOVERNMENT INTEREST

The invention described herein was made by persons including employees of the Department of the Navy who made the invention in performance of official duties. The invention may be manufactured, used, and licensed by or for the Government of the United States of America for governmental purposes without payment of any royalties thereon or therefor. The Government of the United States of America has ownership rights in the invention.

BACKGROUND OF THE INVENTION

The present invention relates to underwater cleaning of hulls of marine vessels such as ships, more particularly to methods and apparatuses for testing and evaluating performance of devices and systems that are implemented for effecting such cleaning.

Air and water quality are negatively impacted by the accumulation of biofouling on ship hulls, which may result for instance in biocide leaching/release, combustion emissions, or translocation of biological species. Biofouling may be mitigated through the use of a combination of underwater hull coatings and in-water maintenance (e.g., hull cleaning).

With respect to vessels with biofouled hulls, in-water cleaning is a cost-effective means of improving operating efficiency and reducing risk of transport of non-indigenous species. Despite the apparent benefits, the in-water cleaning process does not come without cost and does pose some risk both to the biofouling-control coating (antifouling coating) applied to the hull and to the environment. A thin layer of some types of paints is normally removed during in-water hull cleaning. This paint removal can reduce the service life of the hull coating system, and—depending on coating age, coating type, and mechanism of action—may introduce paint components (including biocides) into the environment, especially when the cleaning process does not include a means by which to capture and treat any effluent. The terms "biofouling-control coating" and "antifouling coating" are used interchangeably herein.

Previous efforts have been made to characterize the impact of cleaning tools on coatings such as the biofouling-control coatings on ship hulls. However, these prior approaches were beset with problems and deficiencies, including not adequately replicating or quantifying forces from cleaning head/tool on the coating. They did not allow for quantification of both environmental inputs and impact on paint/coating in a way that takes into account a full-scale application of the cleaning head/tool. Prior methods and techniques were performed with model brushes. They were performed on ships at full-scale where replication and data interpretation were challenging, making the ability to detect small differences in impact on an array of coatings difficult, and where adequate sampling of inputs into the surrounding water was not possible. They were performed on test panels with full-scale tools where adequate sampling of inputs into the surrounding water was not possible.

SUMMARY OF THE INVENTION

The inventive methodology provides apparatus and method for evaluating and quantifying the impact of underwater hull cleaning tools on paint thickness (and thus service life), and on release of paint components such as containing biocides. Exemplary inventive practice allows for measurements of environmental inputs during cleaning, including biocide release (e.g., copper and zinc) and solids/particulate loading. Exemplary inventive practice replicates the function and use of underwater cleaning tools on ship hulls, and allows for precise quantifications of the impacts to underwater paint systems (e.g., in terms of thickness, roughness, damage) and inputs into the surrounding water (e.g., using techniques to collect and chemically analyze water samples). Following exemplary inventive testing, measurements may be made of paint thicknesses and concentrations of paint particles and biocides of interest. Inventively collected data may improve capabilities to predict the effects of hull cleaning on both coating service life and environmental inputs.

In accordance with exemplary practice of the present invention, an inventive apparatus replicates cleaning of a structure in a liquid environment. The inventive apparatus includes a container for a liquid, a cleaning device, and a carrier. The cleaning device includes a cleaning element for contacting a coated planar surface area of a sample. The coated planar surface area is characterized by coating matter situate upon the planar surface area. The carrier transports the sample through the liquid (e.g., seawater) in the container so that the coated planar surface area contactingly moves across the cleaning element while the cleaning element is in a fixed position. The contacting movement of the coated planar surface area across said cleaning material results in release of some of the coating matter into the liquid in the container. According to an exemplary inventive embodiment, the inventive apparatus further includes a driver mechanism, which includes driver wheels. The container includes a tank characterized by a tank length and including trolley-wheel engagement rails along the tank length. The carrier includes a trolley, which includes trolley wheels and driver-wheel engagement rails. The trolley moves in a linear direction along the tank length via engagement of the trolley wheels with the trolley-wheel engagement rails. The driver mechanism impels the trolley via engagement of the drive wheels with the driver-wheel engagement rails. According to an exemplary inventive embodiment, the cleaning device is characterized by rotation of the cleaning element during operation of the cleaning device with respect to the coated planar surface area of the sample. The inventive apparatus further includes a computer, a sensor for measuring speed of the trolley, a sensor for measuring speed of rotation of the cleaning element, and a sensor for measuring torque load characterizing the cleaning device. The computer is implemented for evaluating the release of the coating matter into the liquid during operation of the cleaning device, particularly in terms of correlating sensory measurement values obtained with quantitatively and/or qualitatively analyzed portions of the liquid.

Exemplary practice of the present invention simulates the operating parameters associated with the equipment and processes used during in-water hull cleaning operations. An inventive cleaning tool test device, as exemplarily embodied, simulates the application of cleaning tools to painted surfaces under field conditions, including brush forces and brush rotation and translation rates. For instance, an exemplary test apparatus replicates the application of rotating brushes to a ship hull, including translation rate, rotation rate, and standoff/brush compression. Exemplary inventive practice may include, for instance, evaluation of cleaning tools and commercially available antifouling hull coatings. The tools that are inventively tested and evaluated may include, for instance, equipment currently used by the U.S. Navy to carry out in-water cleaning of ship hulls. Inventive practice may also afford a basis of comparison, in terms of effects on coatings, between legacy cleaning tools and new or emerging cleaning tools.

Exemplary inventive practice enables the evaluation of both the impact of the cleaning tools on the hull coating systems, and the release of substances such as copper and zinc. Exemplary inventive practice takes into consideration conditions representative of the physical conditions present in current hull cleaning practices, including brush forces and rotation and translation rates. Accordingly, exemplary inventive practice assesses the effects of underwater cleaning of hull coatings, including environmental inputs and impact on coating service life, as a function of frequency of cleaning and types of brushes used to carry out the cleaning. Contact cleaning tool elements that admit of inventive practice include but are not limited to brushes (e.g., stiff bristle brushes), cleaning pads (e.g., 3M™ Green scouring/scrubbing pads), sponges, and soft pile carpet pieces. Moreover, the present invention may be practiced in association with nonsolid-contact (e.g., fluid-contact) cleaning tools such as fluid-jet (e.g., waterjet) cleaning heads, as distinguished from solid-contact cleaning tool elements such as brushes (brush filaments), pads, sponges, and carpet swatches. Practically any device or process that involves application of a material to a surface and tends to degrade that surface may be suitable for inventive practice. The applied cleaning element may be solid (steel, composite, textile, natural hair, etc.) or fluid (e.g., water or other liquid cleaning agent).

The present invention, as exemplarily embodied, provides an underwater (UW) ship hull "Cleaning Tool Test Device" (acronymously referred to herein as "CTTD") to evaluate impact of cleaning tools on coating systems, and further provides a method for use of said inventive CTTD. The present inventors have invented, inter alia, a test apparatus and method to evaluate the impacts of hull cleaning tools on coating wear and paint/biocide release. The inventive test apparatus is designed to replicate the application of rotating brushes to a ship hull, including translation rate, rotation rate, and standoff/brush compression. Following the inventive testing, measures of paint thickness and concentrations of paint particles and biocides of interest are possible. The data that is inventively collected will improve the ability to predict the effects of hull cleaning on both coating service life and environmental inputs.

The inventive CTTD, as exemplarily embodied, applies a cleaning device component (for example a cleaning head or brush) to a painted test panel in order to replicate the use/application of the cleaning tool/head at full scale (translation rate, normal and shear forces, rotation rate, pressure, standoff, dwell time, angle and duration). For instance, the cleaning device component would otherwise be designed to remove biofouling from the underwater hulls or propellers/appendages of vessels. Furthermore, exemplary inventive practice enables precise quantification of changes in physical condition of the coating as a result of application of the cleaning device component, and enables collection of water samples in order to quantify inputs of coating components or chemicals into the surrounding water. An exemplary inventive device is configurable, e.g.: configurable to incorporate a wide array of current and potential cleaning tools/cleaning heads; configurable to allow for direct measures of normal and shear forces; and configurable to allow for assessment of biofouling removal. According to exemplary inventive practice, a support structure (e.g., a test stand) is used to support the inventive CTTD in a position above the foundation (e.g., floor or ground).

The present invention's Cleaning Tool Test Device (CTTD), as exemplarily embodied, is designed to enable a standardized process for application of hull cleaning components to biofouling control coatings, and measurement of the impact of these cleaning tool components on the coatings, including physical integrity (in terms of coating thickness, coating scratching, coating removal, coating adhesion failure, etc.) and release of biocides or other coating components as would typically occur during in-water cleaning using tools routinely employed by the U.S. Navy for hull maintenance. To obtain the highest quality data germane to evaluations of various hull cleaning processes, an exemplary inventive apparatus simulates in-water hull cleaning so as to replicate the application of actual cleaning tools, while allowing for collection of water samples for analysis of inputs. Exemplary inventive practice allows for paint thickness measurements to be made in the exact same spot on a painted surface before and after the cleaning tools are utilized. Exemplary use of an inventive CTTD will ensure data precision and accuracy with respect to both (i) impacts upon coatings and (ii) inputs into the environment.

Examples of submerged cleaning systems implemented by the U.S. Navy include the SCAMP™ underwater cleaning system, hand-held single brush cleaning units, and emergent technologies that utilize waterjets. "SCAMP" is an acronym for "Submerged Cleaning and Maintenance Platform(s)." The following United States patents, each of which is hereby incorporated herein by reference, are informative regarding SCAMP-type and other technologies for performing cleaning of underwater surfaces such as ship hull surfaces: Russell Edward Winn, U.S. Pat. No. 3,906,572, issued 23 Sep. 1975; Ben Fond, U.S. Pat. No. 4,011,827, issued 15 Mar. 1977; Ryoji Orita et al., U.S. Pat. No. 4,574,722, issued 11 Mar. 1986; Michael J. Maloney, U.S. Pat. No. 5,222,452, issued 29 Jun. 1993; Michael B. Geiger, U.S. Pat. No. 5,947,051, issued 7 Sep. 1999; Cecil L. Achord, U.S. Pat. No. 6,070,547, issued 6 Jun. 2000; William Martin Hertel, III et al., U.S. Pat. No. 7,971,547 B1, issued 5 Jul. 2011; Kenneth Walter Holappa, U.S. Pat. No. 8,506,719, issued 13 Aug. 2013.

Also of interest herein is David Bartholomew Chadwick et al., "In-Water Hull Cleaning Sampling Method," U.S. Pat. No. 7,444,891, issued 4 Nov. 2008, which is hereby incorporated herein by reference.

BRIEF DESCRIPTION OF THE DRAWINGS

The present invention will now be described, by way of example, with reference to the accompanying drawings, wherein like numbers indicate same or similar parts or components, and wherein:

FIG. 1 shows a basic exemplary inventive arrangement wherein rotating drive wheels move a trolley holding a sample test panel (e.g., coated panel). FIG. 1 also shows a support structure (e.g., table or stand) beneath the inventive CTTD.

FIG. 2 shows a general inventive design wherein the brush and brush drive motor are positioned beneath the trolley, which includes a compartment for holding the sample test panel.

FIGS. 3 and 4 are edge-on and plan views, respectively, of a sample test panel, in particular showing dimensions of the sample test panel, and locations and sizes of mounting holes in the sample test panel, in accordance with an embodiment of the present invention.

FIGS. 6 through 10 are side elevation views of an example of an inventive CTTD, along with a support structure associated therewith. Considered together in sequence, FIGS. 6 through 10 diagram an example of inventive operation wherein a trolley (carrier) moves across the top of a cleaning tool so that, through part of the trolley's traversal, a test sample (e.g., a coated panel housed in the trolley) is above and in contact with the cleaning element (e.g., cleaning brush filaments, cleaning pad, or waterjet pulse) of the cleaning tool.

FIG. 13 is a top perspective view of the inventive CTTD and support structure shown in FIG. 11, particularly pointing out plumbing interfaces (inlet and outlet) for the inventive CTTD, and diagrammatically illustrating transmission of various sensory signals to a computer.

FIGS. 14 through 18 are top perspective views of a trolley such as shown in FIG. 11. FIGS. 14 and 16 through 18 show a test sample contained in the sample-holding compartment of the trolley. FIG. 15 is a partial view showing the sample-holding compartment sans test sample. FIGS. 17 and 18 show the sample-holding compartment lifted, in an upwardly rotated position.

FIGS. 19 through 22 are top perspective views of the inventive CTTD and support structure shown in FIG. 11, particularly illustrating a safety shield (splash guard) over the cleaning brush installation, for use during operation of an exemplary inventive CTTD.

FIG. 25 shows the upper limit of the adjustable standoff, wherein the brush is closest to the sample test panel thereabove.

FIG. 26 shows the lower limit of the adjustable standoff, wherein the brush is furthest from the sample test panel thereabove.

As shown in FIG. 27, the brush element is proximate the test panel.

DESCRIPTION OF EXEMPLARY EMBODIMENTS OF THE INVENTION

Referring now to the figures, an exemplary inventive Cleaning Tool Test Device (CTTD) is designed to standardize the measurement of coating wear and biocide release from paints, as would occur during in-water cleaning of marine hulls. The inventive device may use, for example, tools that are routinely employed by the U.S. Navy for hull maintenance, such as brush cleaning units that may be associated with the underwater cleaning system known as "SCAMP," or hand-held single brush cleaning units. The exemplary inventive test device is modular in design to additionally enable the evaluation of emergent cleaning technologies (such as those that utilize waterjets).

Figure 1:
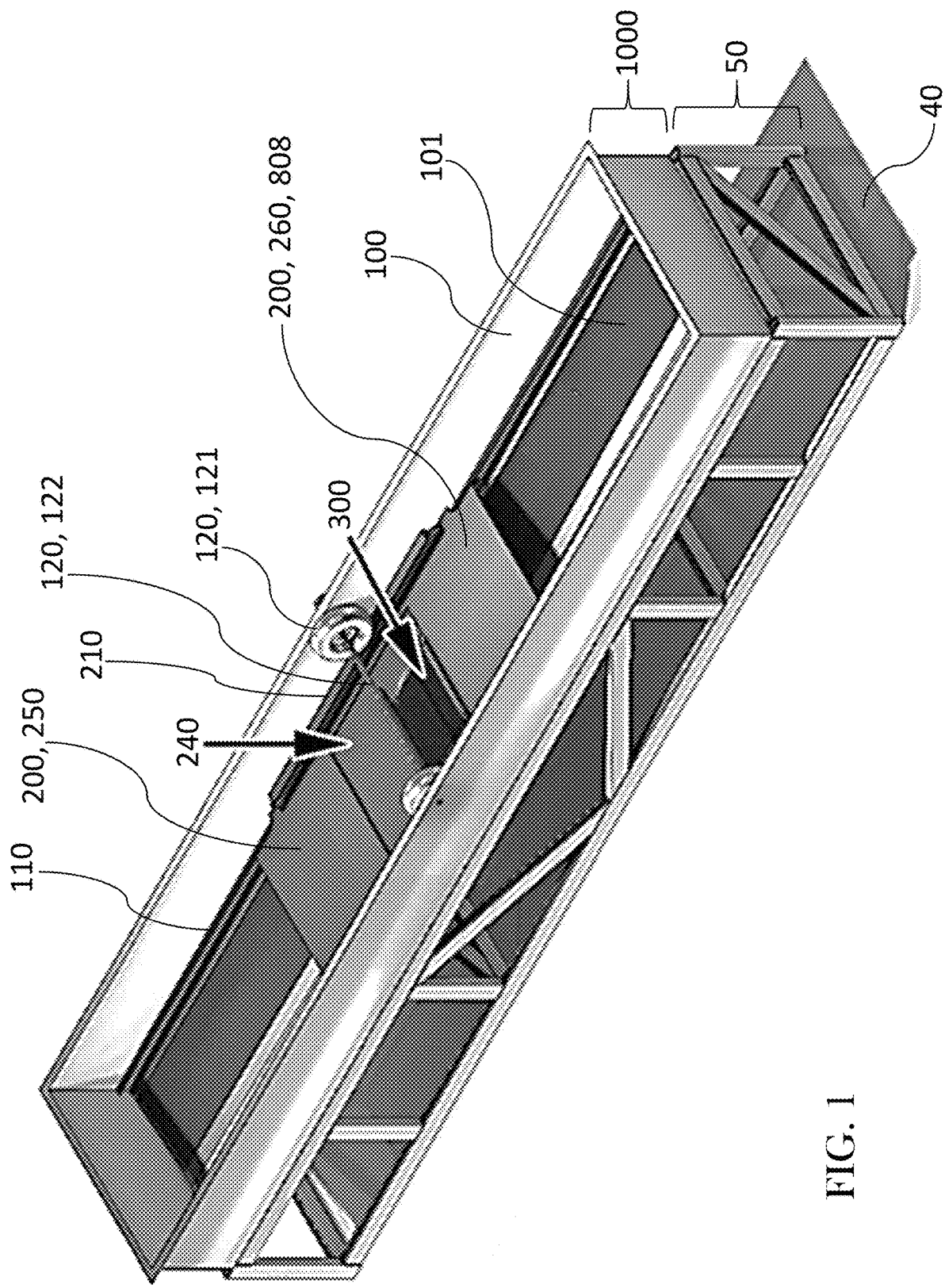
FIG. 1 is a top perspective view of an exemplary Cleaning Tool Test Device (CTTD) in accordance with the present invention.
Figure 2:
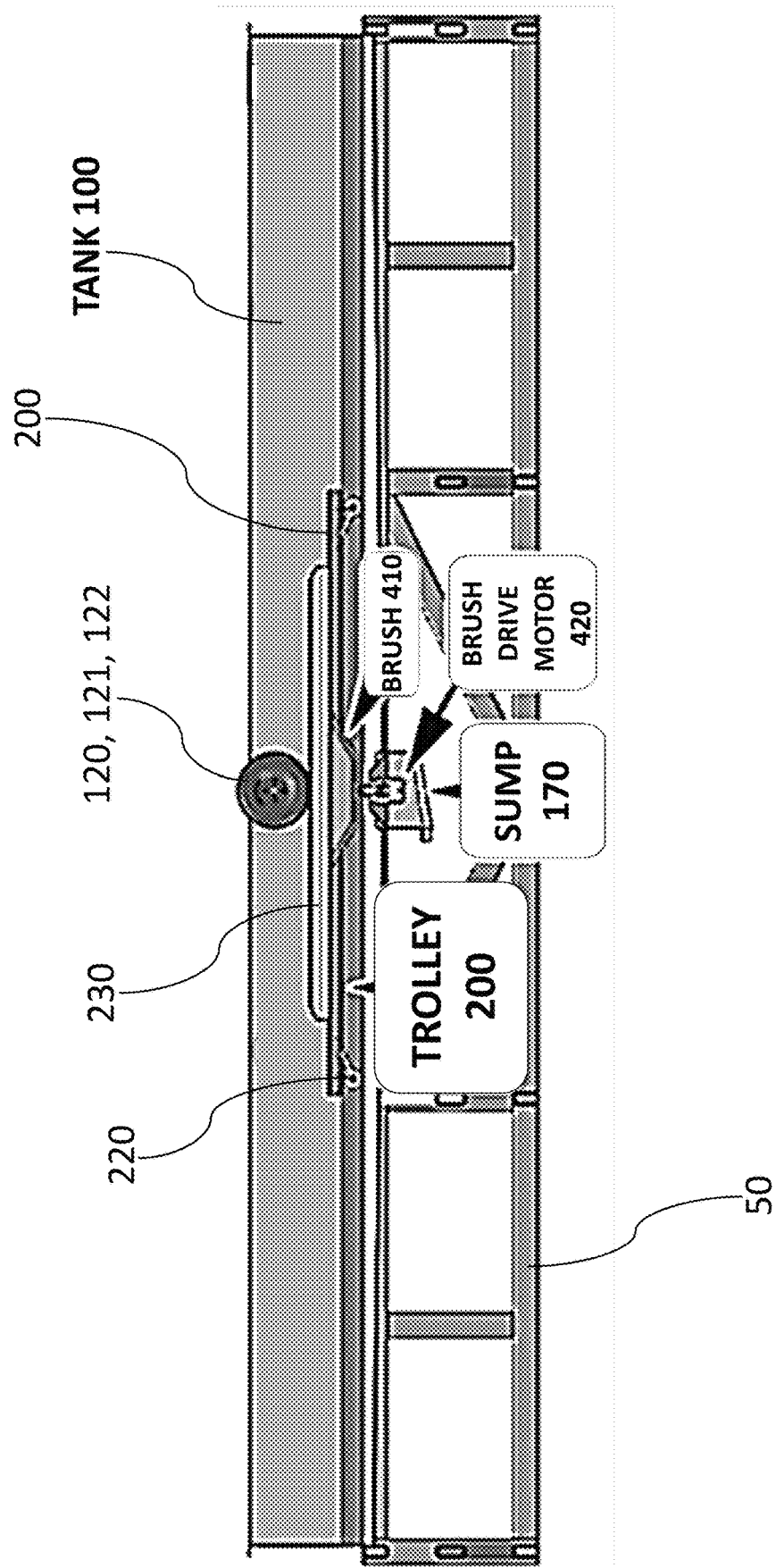
FIG. 2 is a side elevation view of the inventive CTTD and its support structure as are shown in FIG. 1. In particular.

As shown in FIGS. 1 and 2, an exemplary inventive CTTD 1000 includes a tank 100, a pair of trolley-wheel engagement rails (tracks) 110, and a trolley 200. Trolley-wheel engagement rails 110 are, to at least a substantial degree, straight and parallel to each other. Tank 100 generally describes a rectangular parallelepiped shape and includes an at least substantially rectangular tank bottom 101. Trolley 200 has a trolley frame 210 and four trolley wheels 220, and is provided along its longitudinal side edges with a pair of translation drive drive-wheel engagement rails (tracks) 230 for respectively engaging the two drive wheels 121. Trolley frame 210 is stiff to ensure standoff under load. The tank's trolley-wheel engagement rails 110 support trolley 200 while contacting trolley wheels 220, the rails 110 thus serving as tracks for travel (rolling on trolley wheels 220) by trolley 200, which holds the sample 300.

Trolley 200 is propelled along trolley-wheel engagement rails 110 by a drive mechanism 120 that includes a pair of rotatable drive wheels 121, an axle 122 connecting drive wheels 121, and a hydraulic translation drive motor 123 for powering drive mechanism 120. Drive mechanism 120 imparts movement to trolley 200 via mechanical interaction of the drive mechanism's drive wheels 121 in contact with the trolley's drive-wheel engagement rails 230, which to at least a substantial degree are straight and parallel to each other. Trolley 200 moves linearly over the cleaning element 410 (e.g., cleaning brush bristles or other brush filaments) in such a way as to replicate the conditions of either a SCAMP-type cleaning system, or a hand-held brush cleaning system, or a similar cleaning system passing over the hull of a ship. It can be considered that trolley 200 is part of a carrier unit 808, which includes trolley 200 and may also include one or more other components that are combined with trolley 200.

With reference to FIGS. 3 and 4, the test sample 300 is for example a coated steel panel and is utilized to represent a ship hull. According to this exemplary inventive embodiment, the coated steel sample panel 300 includes a flat steel panel substrate 310 having dimensions 18"x18"x0.125", and a coating 320 having nominal coating thickness of 0.027". For instance, to make a test sample 300 of interest, a planar substrate 310 is painted with an antifouling coating of interest 320. By way of example, the sample panel 300 is exposed to natural seawater for one-to-two months to allow for stabilization of biocide release rate and development of fouling by, at minimum, biofilms. In order to quantify wear associated with cleaning, coating (e.g., paint) thickness can be measured before and after application of the cleaning tool(s) to the coated panel 300.

Figure 5:
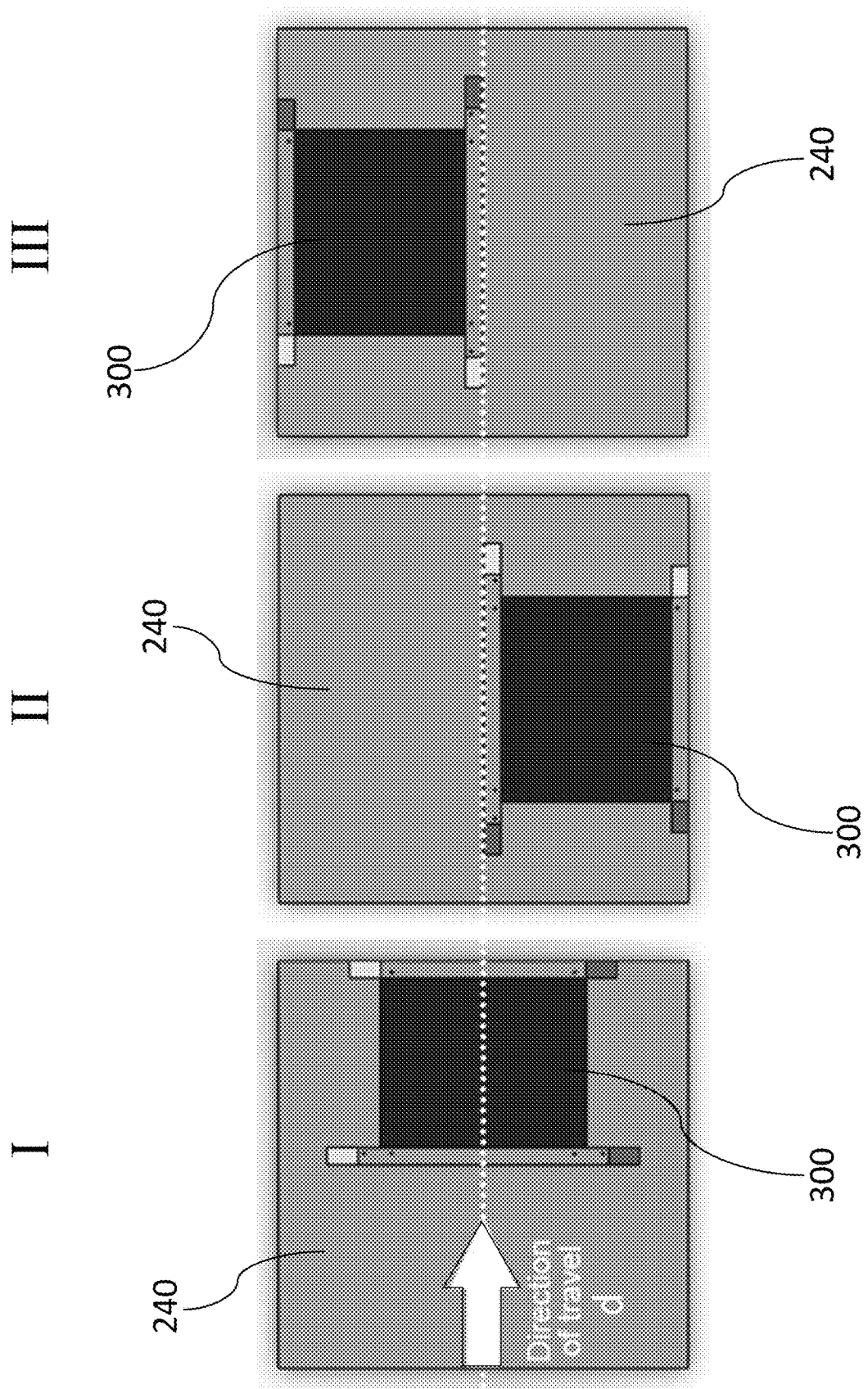
FIG. 5 is a plan view diagramming, by way of example, three different positions at ninety-degree rotations of a sample test panel situated in the sample-holding compartment of a trolley.
Figure 11:
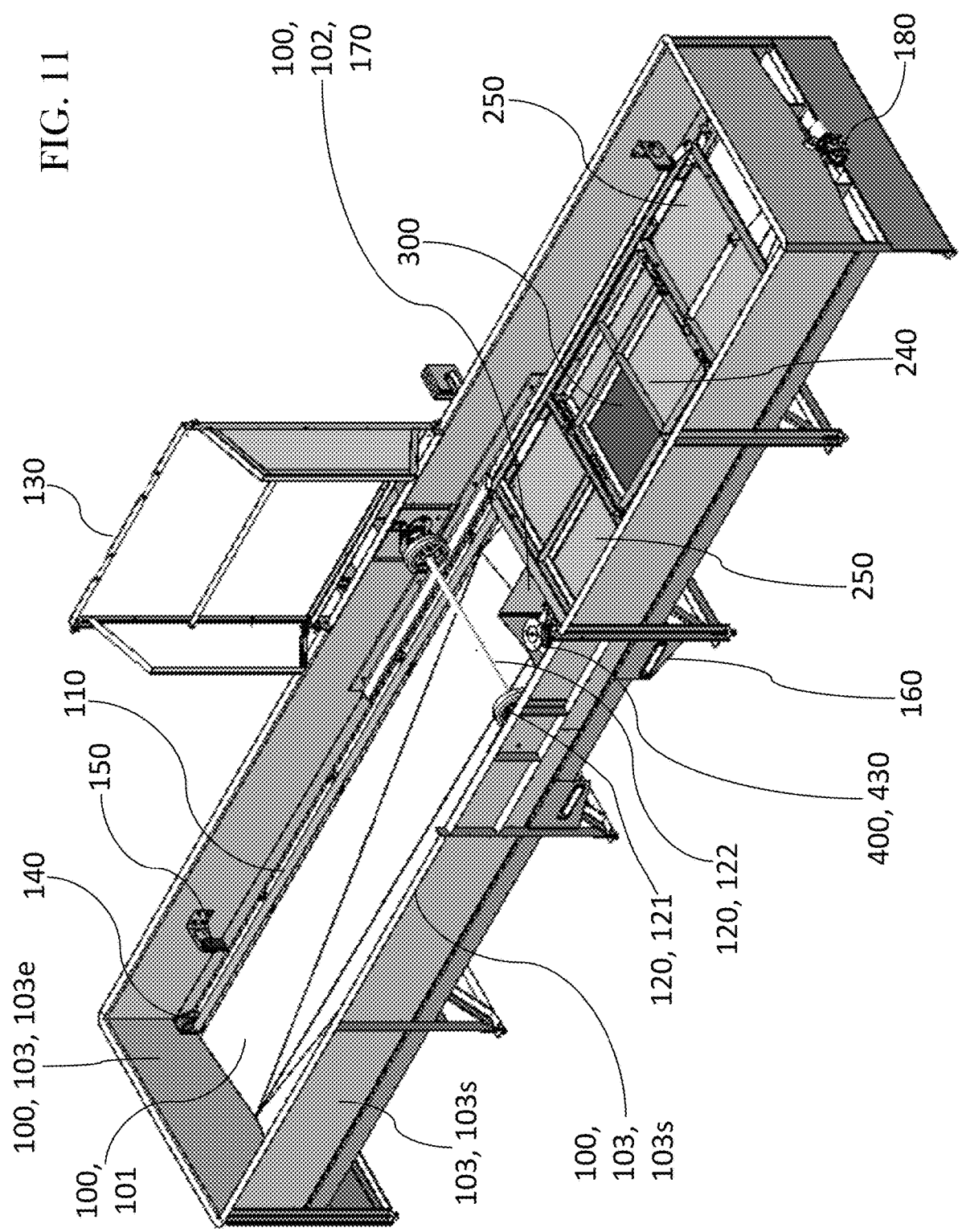
FIG. 11 is a top perspective view of an example of an inventive CTTD (along with its support structure) that is similar to the inventive CTTD shown in FIG. 1.

As shown by way of example in FIG. 5, the lateral position of the sample 300 is maintained by a sample holder 240 attached to or mounted on trolley 200. Sample holder 240 can be designed to hold sample 300 in any lateral position within the width of the trolley 200. Sample 300 can easily be positioned in any of three discreet lateral locations wherein the centerline of sample 300 is 0 inches, −9 inches, and +9 inches from the centerline of tank 100, by rotating sample holder 210 to be situate at angles 0°, −90°, or +90° degrees relative to the direction of forward motion d of trolley 200. Should other positions of sample 300 be required, a new or modified sample holder 240 may be used to position sample 300 in any position up to 9 inches from the centerline of travel d.

Sequential trolley-travel operation of an exemplary inventive CTTD 1000 is illustrated in FIGS. 6 through 10. Trolley 200 includes adjustable wear plates 460 and 450, which act as lead-in and lead-out plates to properly compress the cleaning element 410. The brush assembly 400 and the sample 300 are mounted into the inventive device 1000, and either the trolley 200 or the brush 410 is adjusted to the proper standoff height of the sample 300 surface vis-à-vis the brush 410 (FIG. 6). Trolley 200 and cleaning (e.g., brush) assembly 400 are each at least partially submerged in saltwater SW. Sample 300 and cleaning material (e.g., brush filaments) 410 are each completely submerged in saltwater 300. When ready to test, the operator slowly maneuvers trolley 200, situate in tank 100 and at least partially submerged in saltwater SW, until trolley rails 230 contact the translation drive wheels 121 (FIG. 7). At this stage the cleaning material 410 is in contact with the lead-in wear plate 460. The operator engages the inventive test system 1000, and the drive wheels 121 pull the trolley 200 over the brush 410, trolley 200 thereby moving in direction d. Cleaning material 410 contacts sample 300 (FIG. 8) and then contacts lead-out wear plate 450. Trolley 200 thereby moves in direction d until the drive wheels 121 are no longer in contact with the trolley rails 230, when trolley 200 has transited fully to the other side (FIG. 10). The operator then disengages the inventive system.

With reference to FIGS. 11 through 24, tank 100 (e.g., made of aluminum or stainless steel) includes four walls 103 (i.e., longitudinal side walls 103s and widthwise end walls 103e) and a "raceway-style" tank bottom 101 provided with an opening 102, which corresponds and permits access to sump 170 below. In effect, the tank's opening at the bottom of the tank is the sump's opening at the top of the sump, wherein the sump is situate beneath the tank. Tank 100 has associated therewith a pair of trolley-wheel engagement rails 110, a translation drive mechanism 120, a safety shield 130, four corner bumpers 140, brakes 150, fork pockets 160, a sump 170, a tank inlet valve 180, and a sump outlet valve 190. Tank bottom 101 is angularly configured to slope downward for encouraging fluid flow toward and into sump 170. Sump 170 has a sump bottom 171 that is angularly configured to slope downwardly in a tank-longitudinal direction for encouraging fluid flow toward and out into sump outlet 190.

Figure 12:
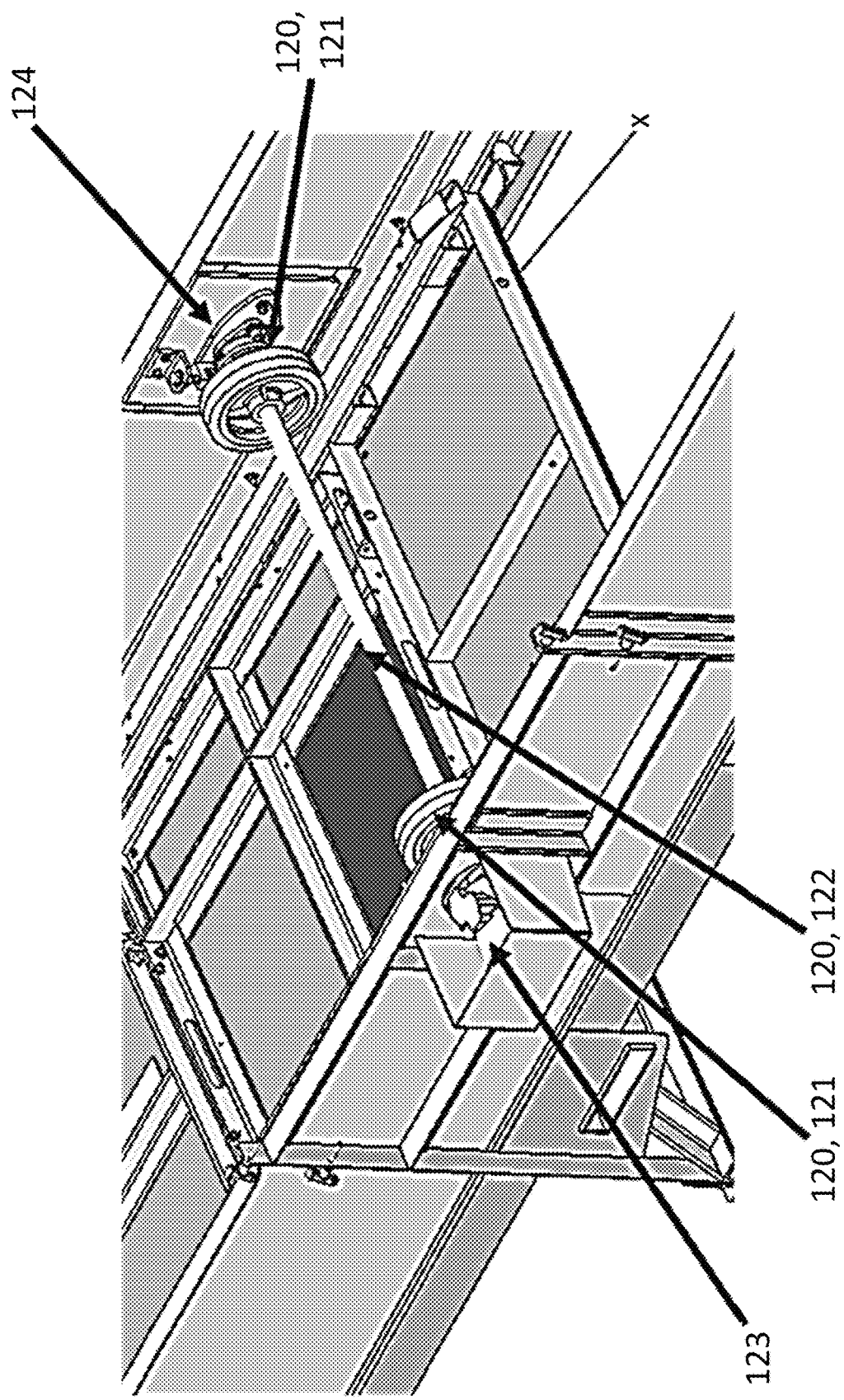
FIG. 12 is a partial and enlarged perspective view of the inventive CTTD shown in FIG. 11.
Figure 16:
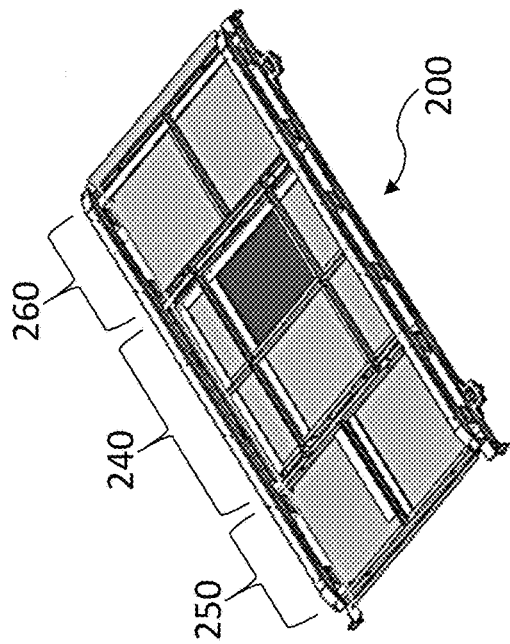
Figure 18:
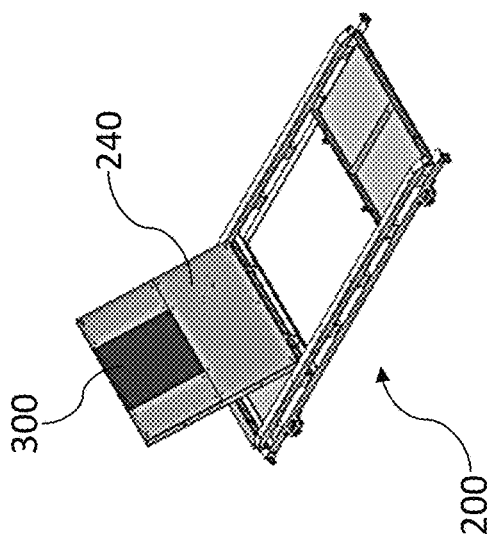
Figure 15:
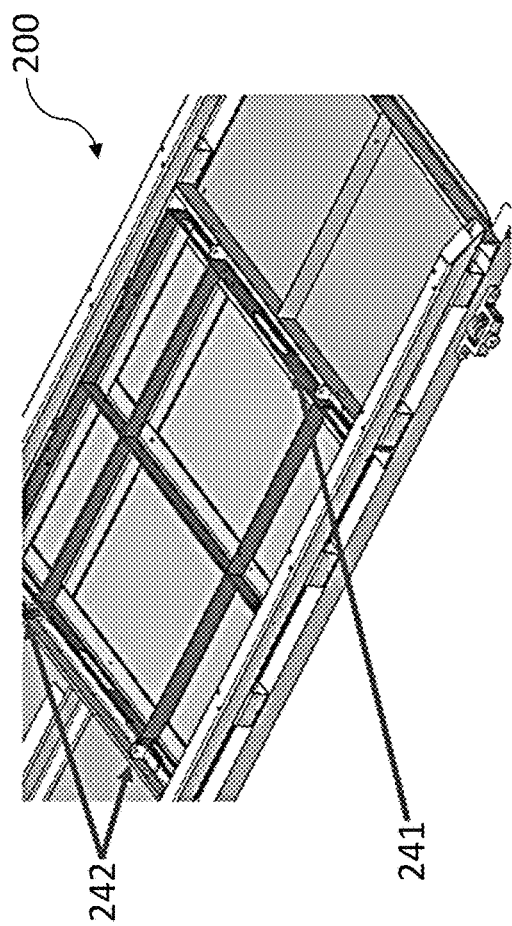
Figure 17:
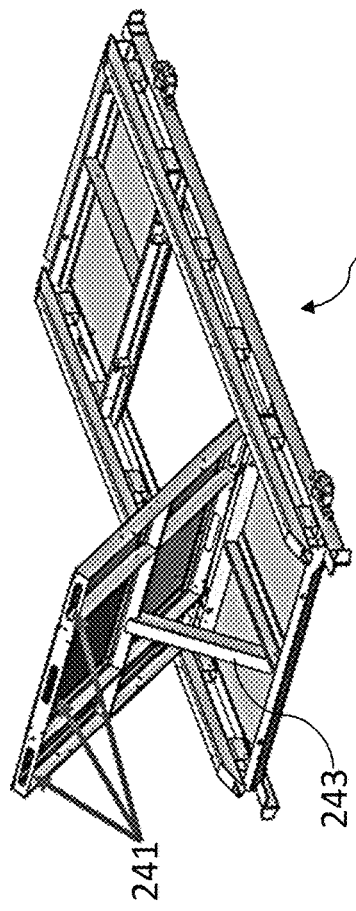

Bumpers 140 are positioned at or near the ends of the tank rails 110 to assuage impacts that may occur between trolley 200 and tank 100. Sump 170 is a receptacle, attached to or built into tank 100, for containing some saltwater SW and for encompassing at least part of the cleaning brush assembly 400, especially hydraulic drive motor 420. Since tank 100 and sump 170 together contain the saltwater SW, it may be considered that tank 100 and sump 170 together constitute a container 909 for containing saltwater SW. As shown in FIG. 12, translation drive mechanism 120 includes a pair of drive wheels 121, an axle 122, a translation drive motor 123, and a translation drive height adjustment bracket 124. As shown in FIGS. 19 through 22, safety shield 130, rotatable upward as well as downward over the cleaning brush head 410, includes shield hinge pins 131 and shield safety pins 132. Fork pockets 160 are attached to the tank 100 and/or the tank's stand 50 to facilitate lifting of the inventive apparatus 1000, together with the stand 50, off the foundation (e.g., ground or floor) 40.

Figures 27, 28:
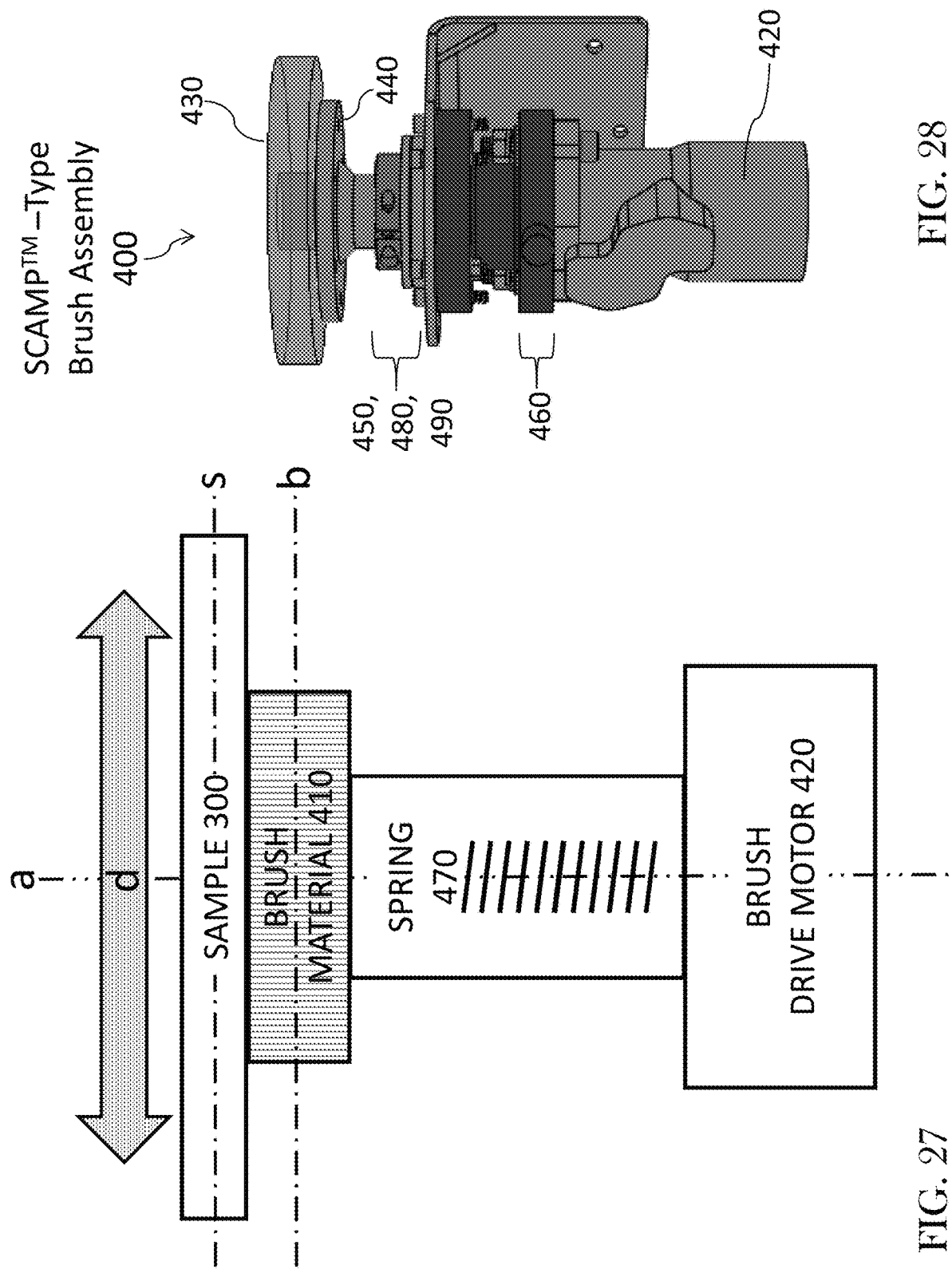
FIG. 27 is a schematic of some basic components of a hull surface cleaning apparatus in relation to a sample test panel.
FIGS. 28 through 30 depict, by way of example, various brush assemblies that may be suitable for inventive practice. Shown are a SCAMP-type brush assembly (FIG. 28), a hand-held brush assembly (FIG. 29), and a spring brush assembly (FIG. 30).
Figure 30:
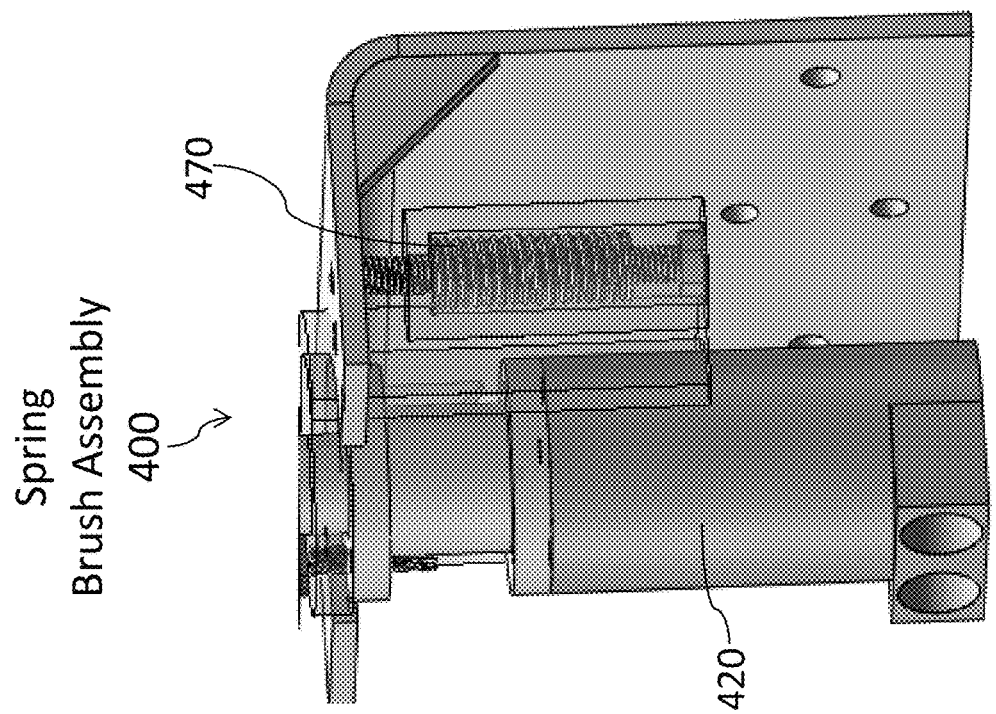
Figure 29:
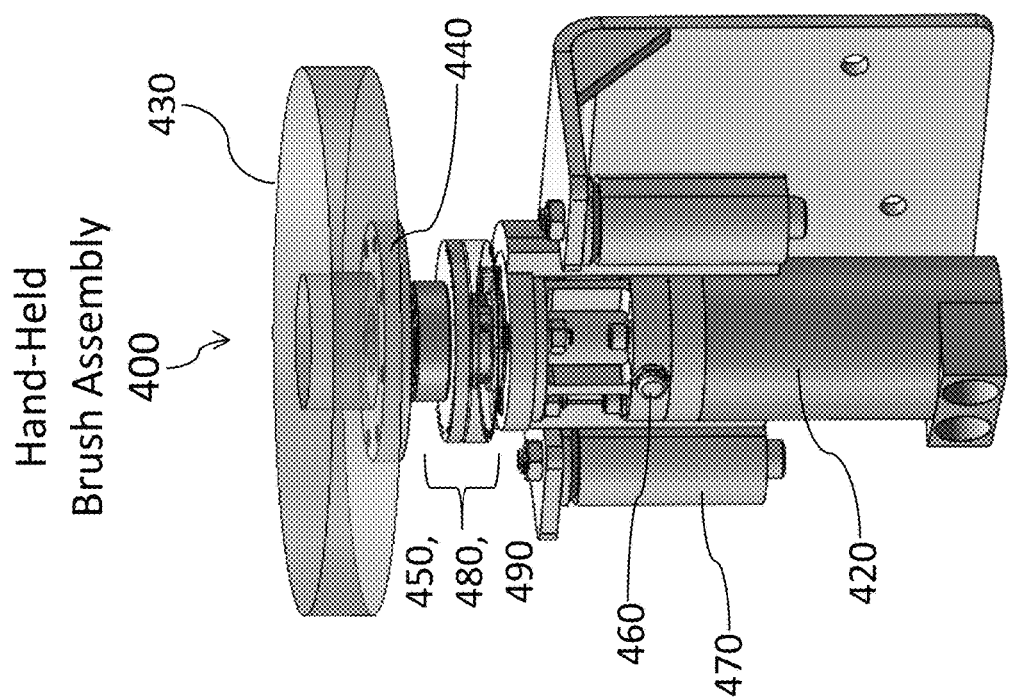

With reference to FIGS. 25 through 30, a cleaning brush assembly 400, which includes brush 410 and hydraulic brush drive motor 420, is located in sump 170 at the bottom of tank 100 and faces upward, thereby facilitating changing of brushes or cleaning heads. Cleaning brush assembly 400 includes brush 410, hydraulic brush drive motor 420, brush hub 430, motor hub 440, brush (e.g., rotational) speed sensor 450, brush torque load sensor 460, compression spring 470, rotor 480, and stator 490. FIG. 27 is basically and exemplarily representative of implementation of cleaning apparatus for conducting testing in accordance with the present invention. Direction d of the motion of trolley 200, also illustrated in FIGS. 5 through 10, accords with the geometric longitudinal bisector of trolley 200, which generally describes a rectangular profile. The contacting portion at the top of cleaning brush 410 is characterized by a horizontal geometric plane b, and the sample 300 is characterized by a horizontal geometric plane s which is parallel to geometric plane b. Brush assembly 400 is characterized by a vertical axis a, which is the axis of rotation if brush assembly 400 is embodied as a rotary brush device with brush 410 rotatable about axis a. Depending on the inventive embodiment, translation drive mechanism 120 may power either unidirectional or bidirectional motion of trolley 200 in direction d.

Figure 26:
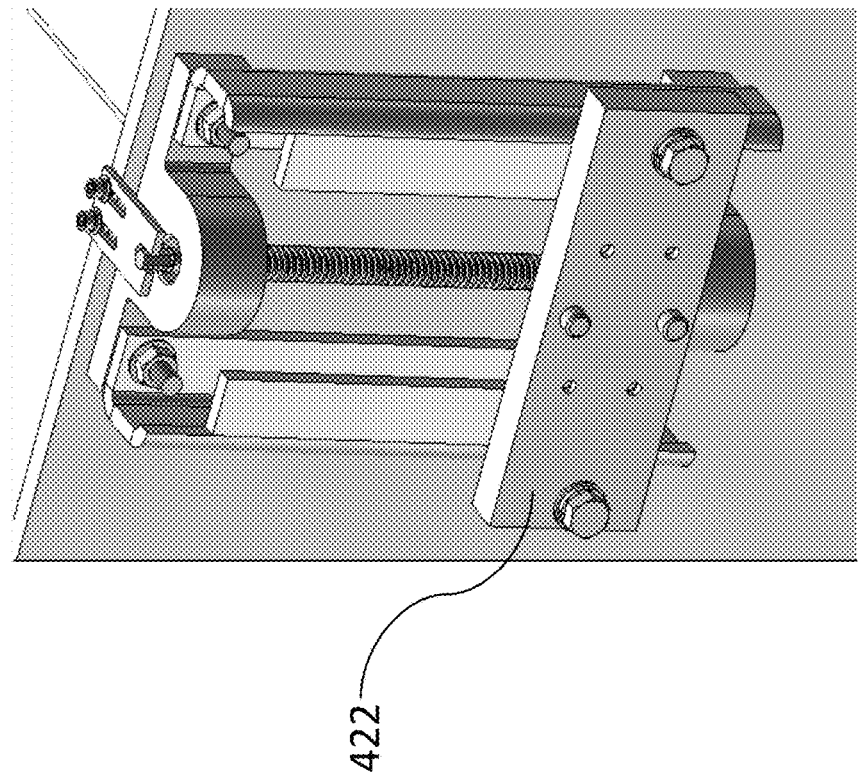
FIGS. 25 and 26 are perspective views illustrating vertical bidirectional adjustability of the positioning of the brush motor mount.
Figure 25:
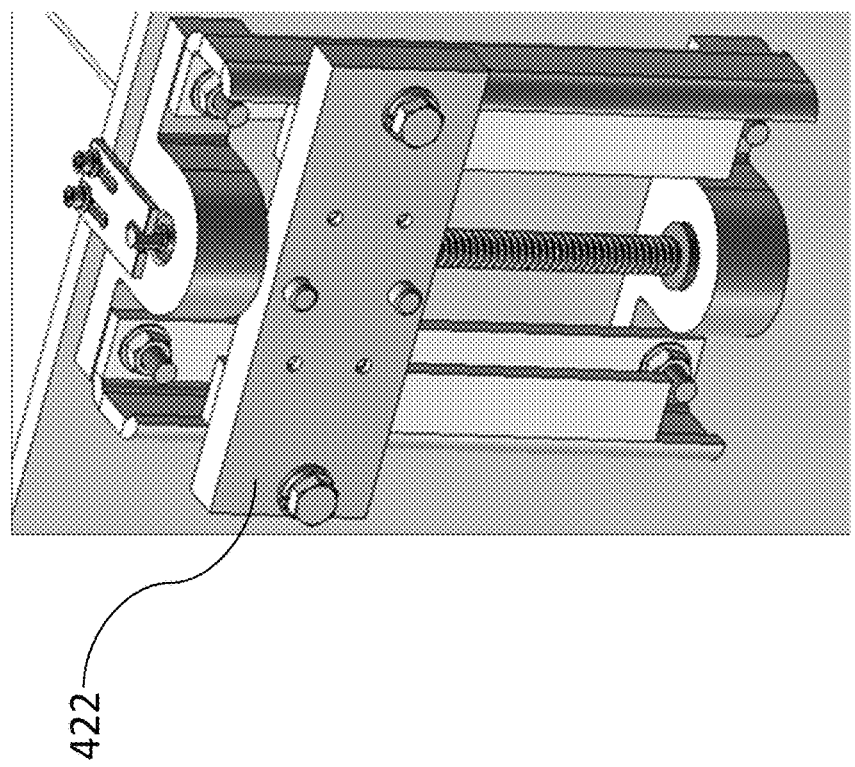

Hydraulic brush motors 420 may be same as or similar to those for instance used in SCAMP-type systems (such as a SCAMP™ system manufactured by Seaward Marine Services, LLC) or in hand-held cleaning tool systems. The brush cleaning system 400 is powered by a Hydraulic Power Unit (HPU) 420 and controlled through manual hydraulic valves 421 (e.g., through-hull quick connect hydraulic fittings), at least one hydraulic valve 421 connecting to each motor 420. Speed sensors are included for both the trolley and the brushes, i.e., trolley speed sensor 270 and brush (e.g., rotational) speed sensor 450. In addition, a torque load sensor 460 measures the load on the brush 410. As shown in FIG. 13, measurement data signals from sensors 270, 450, and 460 are acquired on a computer 500 (such as a laptop computer) and are available for later evaluation. As shown in FIGS. 25 and 26, a brush motor mount 422 affords adjustable standoff of brush 410 with respect to the coated bottom surface of sample 300.

Figure 23:
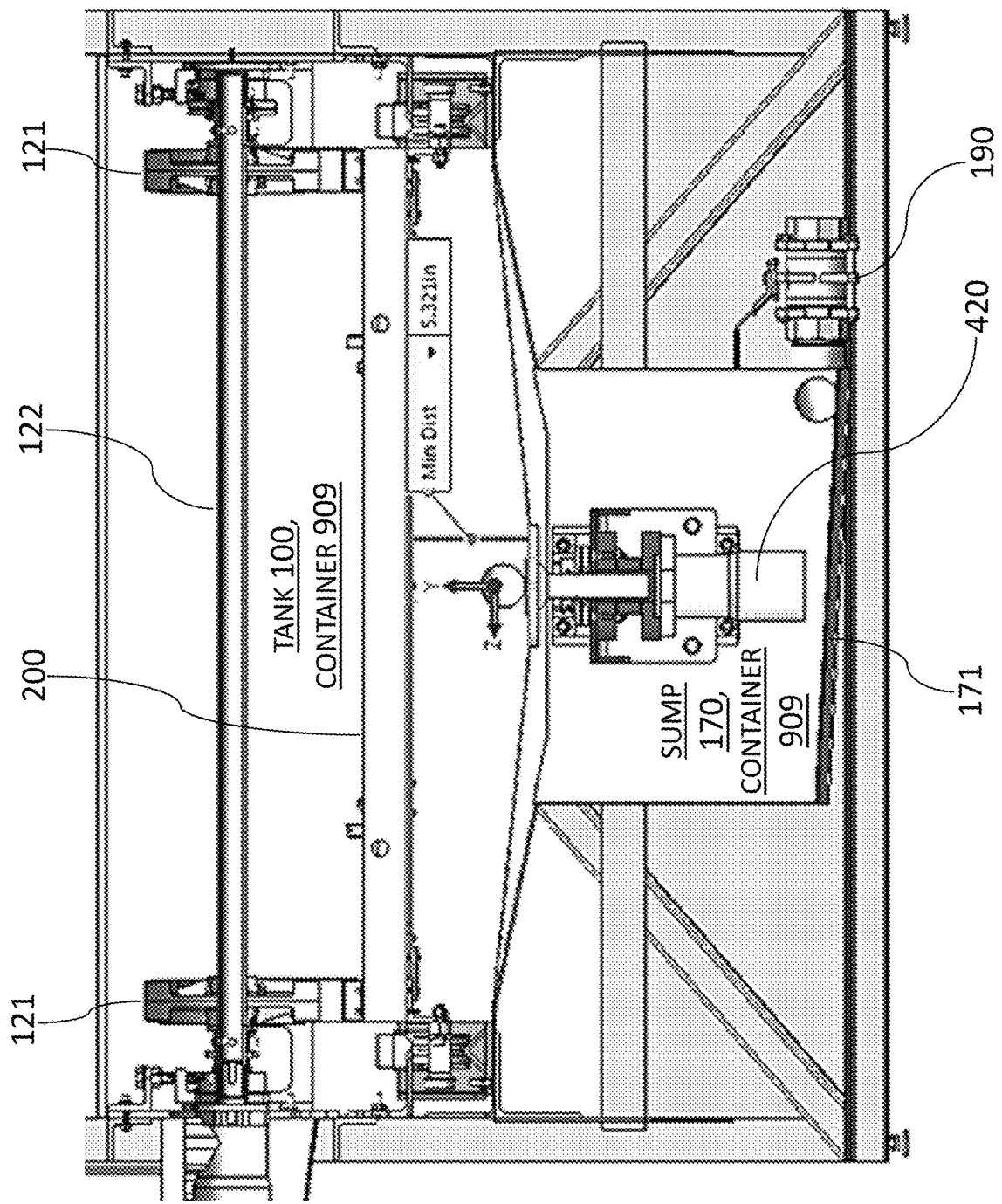
FIG. 23 is a cross-sectional side elevation view of an inventive CTTD such as shown in FIG. 11, particularly showing a sump, a brush motor mounted in the sump, and an outlet valve.
Figure 24:
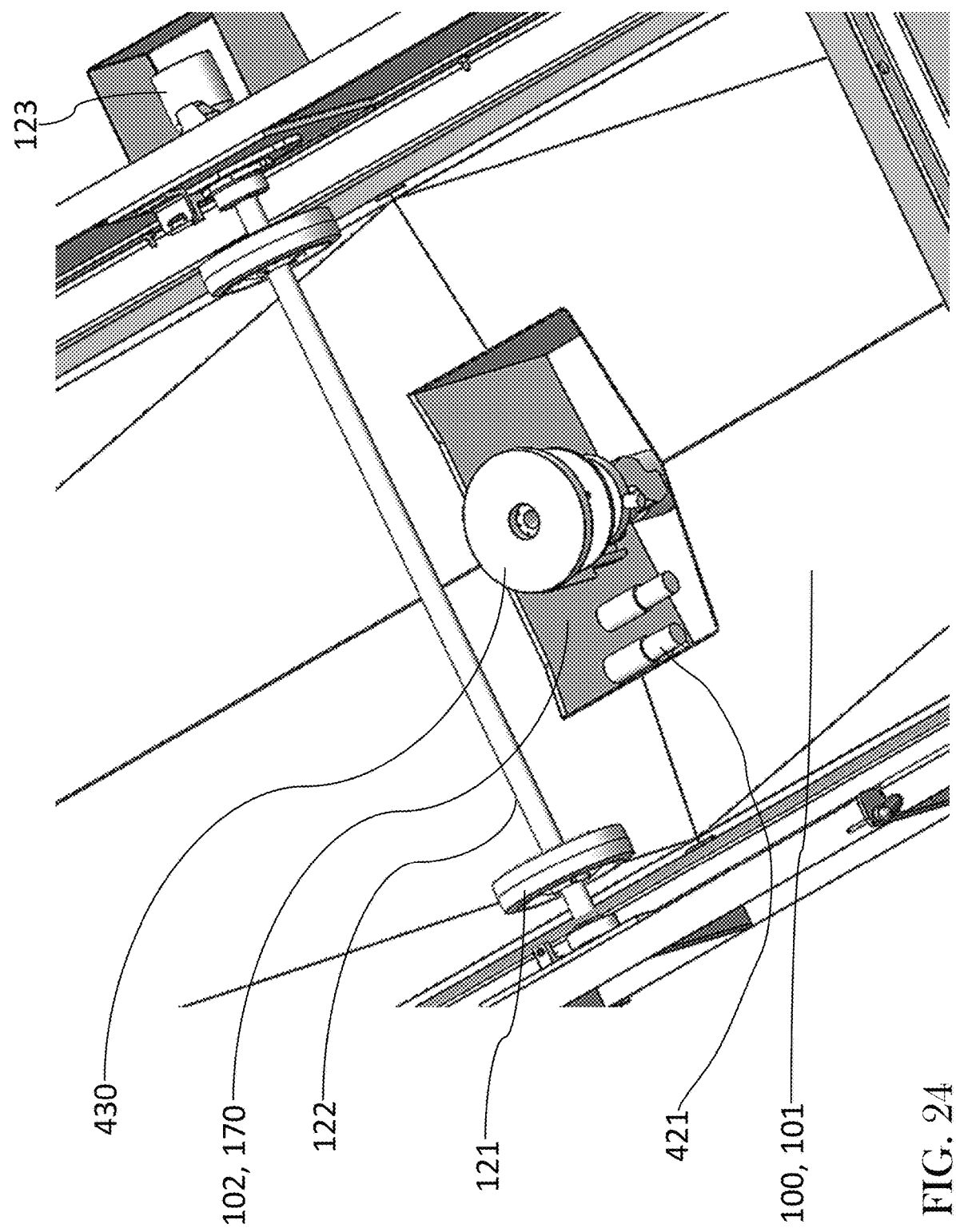
FIG. 24 is a partial top perspective view of an example of the tank and some other components of an inventive CTTD, particularly showing the brush motor mounted in the sump, and the through-hull quick-connect hydraulic fittings protruding in the sump, for actuation of the brush motor.

Water samples can be retained for analysis to quantify contaminant loading as a function of cleaning. The saltwater SW contained in tank 100 can be sampled for analysis of biocide inputs, or the entire contents of the tank drained through the drive motor sump outlet valve 190 and filtered, for analysis of solids. Note in FIG. 11 the nonplanar shape of the raceway bottom 101 of the test tank 100, designed to allow easy draining of the tank 100 (e.g., for sample collection) through the drive motor sump 170. Sump 170 is shown in FIG. 23 by way of example, as inventive practice is possible wherein the sump is characterized by a variety of sizes, shapes, and dimensions. According to some inventive embodiments, a sump is configured to accommodate other tools.

An exemplary inventive CTTD is designed using materials that minimize corrosion and interference with chemical and solids analyses that will be performed on water samples collected during testing. It is also designed to minimize the amount of water required for testing and disposal, and to facilitate quick and complete draining and system cleaning. An exemplary inventive CTTD is designed, built, and tested to be in compliance with relevant safety and health standards including Occupational Safety and Health Administration (OSHA) and applicable consensus standards such as those issued from the American National Standards Institute (ANSI), American Society for Testing and Materials (ASTM), or similar.

An exemplary inventive device is able to be shipped by truck to any installation facility. An exemplary inventive device replicates, for instance, cleaning of a flat hull section in accordance with a SCAMP-type cleaning system, and/or cleaning thereof by a hand-held single-brush cleaning unit. An exemplary inventive device accommodates evaluations using the different brushes employed in accordance with the SCAMP-type cleaning system, and/or the hand-held single brush cleaning unit. According to some examples of inventive practice, brushes range in size from 9"-23" in diameter, and are approximately 8" in height. When compressed during operations, brush diameter may be as much as 25". An exemplary inventive device allows cleaning brushes to be easily removed or replaced.

An exemplary inventive device can accommodate a single test sample 300, for instance a test sample consisting of a coated steel panel (18"x18"x0.125", nominal coating thickness 0.027") as shown in FIGS. 3 and 4. An uncoated panel 310 can be coated (e.g., painted) with a test coating 320 of interest, and exposed to appropriate immersion conditions for a designated length of time before testing in the inventive device 1000. The sample test panel 300 is shown in FIGS. 3 and 4 by way of example, as inventive practice is possible for sample test panels of various dimensions. According to some inventive embodiments, two or more test samples can be tested simultaneously.

An exemplary inventive device is capable of being completely drained and refilled through 2" NPT fittings, in order to facilitate sample collection and set-up for subsequent tests. An exemplary inventive device is designed so as to minimize volume in order to reduce water usage and draining/refilling time. An exemplary inventive device is designed to minimize corrosion as well as introduction of any chemicals into the sample water that might interfere with measurement of biocides, repellents, or other compounds associated with the coating systems being evaluated. Operation of an exemplary inventive device does not introduce significant amounts of air (through suction or vortex generation) into the area where the cleaning brush contacts the test sample. An exemplary inventive device allows transit of the cleaning brushes across the test sample at user-controlled rates between 0.1 ft/s and 1.0 ft/sec.

An exemplary inventive device allows for rotation of cleaning brushes at a range of speeds. For testing of SCAMP brushes the desired rotation rates are between 100-130 rpm unloaded, and in air. For testing of brushes used on the hand-held system the desired rotation rates are between 650-950 rpm unloaded, and in air. The torque capability of the brush motor matches the capability of the SCAMP and hand-held systems. Torque capability is determined by the maximum available pressure applied to the respective hydraulic motors. For the SCAMP system, torque capability matches the SCAMP brush motor with 1700 psi applied to the motor. For the handheld system, the torque capability matches the handheld system with 2000 psi applied to the motor. During operation of an exemplary inventive device, brushes being used impart, to the test sample, shear and normal forces comparable to those imparted to a ship hull during in water cleaning. This is accomplished by employing the same operating conditions (e.g. transit speed, rotation rate of brushes, standoff of the brush to the test sample, etc.) as the actual tools. The standoff distance from the brush hub to the surface of the test sample is adjustable from 1" to 4". The brushes also have the capability to be free floating.

As shown in FIGS. 13, 26, and 27, exemplary inventive apparatus incorporates sensors in order to record operational data such as brush rotation rate (RPM), brush torque, and brush translation rate. Brush rotation rate is measured from 100-1000 RPM at an accuracy of +/−2% of full scale. A torque sensor is installed, capable of measuring the entire range of torques generated by the brush motor, with a 50% safety factor. Brush torque is measured up to the maximum torque of the brush motor at an accuracy of +/−2% of full scale. Brush translation rate is measured over the entire operational range to an accuracy of +/−2% of full scale. An exemplary inventive device is capable of recording sensor readings to a computer, such as computer 500 diagrammatically represented in FIG. 13, at a minimum of 4 Hz for test durations of 1 min or less.

An exemplary inventive device includes a ruggedized laptop with either COTS data acquisition software for digitizing and logging sensor data or custom software built using either Matlab or Labview. The software is able to output comma-delimited text files of the logged sensor data. Two types of electrical power are supplied to the inventive device, viz., 3 phase, 460 VAC (60 Hz), 30 Amps for the hydraulic motors, and single phase, 120 VAC (60 Hz), 20 Amps for the sensors, controls, and data-logging equipment. The inventive device incorporates a lockout feature or features to prevent unauthorized startup of the hydraulic power unit. The inventive device meets machine safeguarding standards to prevent exposure to point-of-operation hazards.

In order to inventively measure coating loss and environmental inputs associated with in-water cleaning, antifouling coatings are applied to steel panels to make a test sample. As depicted shown in FIG. 4, test sample 300 is a coated panel 300 including a flat (e.g., steel) panel 310 and a coating 320. Coating thickness, as dry film thickness (DFT), is measured after coating (e.g., painting) and before exposure using standard procedures and equipment (e.g., appropriate sampling scheme, paint thickness gauge, waterproof probe). Coated panels are then immersed in a biofouling environment for at least two months, at which point biocide release from the coating matrix, and thus interaction of the paint surface with the local environment, has typically stabilized. After two months of exposure, panels to be subjected to cleaning are removed from the water, and paint thickness measured using standard procedures and equipment. Panels are then mounted in the inventive CTTD and cleaned using the brush, brush head, or tool type of interest.

Upon completion of the cleaning process, the panel is removed from the inventive CTTD, and paint thickness is measured using procedures and equipment such as those standardized and known in the art. Coating thickness loss upon cleaning is quantified by comparing dry film thickness measurements taken after cleaning to those taken before application of the cleaning tool. Statistical significance of thickness change, and variation in thickness change among cleaning tools, can be determined using standard statistical methods (depending on data quality). According to exemplary inventive practice, biocide release associated with cleaning is measured from water samples taken from the inventive CTTD, and can include analysis for dissolved and total copper and zinc, for example. Analyses of extracted water portions may involve consideration of any of multifarious items that may be germane to an assessment of the effects of the cleaning.

Prior to each test event, the brushes, brush heads, or cleaning tools to be used are rinsed, such as with high-purity (18 MΩ·cm) water. By way of inventive example, equipment blanks (n=3) and appropriate initial treatment seawater blanks (n=3) are collected. The exemplary inventive CTTD is thoroughly rinsed and then filled with filtered natural seawater, or with suitable artificial seawater, to the designated level. For instance, 5 μm filters may be used for filtration of natural seawater. By way of example of inventive practice, once the appropriate panel is treated in the inventive CTTD by the prescribed cleaning tool, the entire seawater volume is mixed as thoroughly as possible, and a 60 mL aliquot of seawater is collected for total metal quantification. Next, a 25 mL aliquot is collected and filtered through a 0.45 μm disc filter to be used to measure the dissolved component of the metal of interest. The remaining seawater in the inventive CTTD is filtered through a previously weighed 0.45 μm filter for measurement of the mass of particulate material generated during cleaning.

In accordance with exemplary inventive embodiments, in order to assure the reliability of the results, metal content analysis is subjected to quality assurance/quality control (QA/QC) that is stricter than that recommended by the U.S. Environmental Protection Agency (US EPA). Both the dissolved and total samples are acidified to pH 52 with quartz still-grade nitric acid (Q-HNO$_3$) in a High Efficiency Particulate Air (HEPA) class-100 all polypropylene working area. Metal concentrations are quantified following the procedures in US EPA's Method 200.8 (US EPA 1994) for trace elements in waters, by inductively coupled plasma mass spectrometry (ICP-MS). Besides following trace metal clean techniques (US EPA 1996) and the full QA/QC approach recommended by US EPA, the analysis includes standard reference materials every 20 samples for verification of the metal concentration, with acceptable QA/QC of recoveries within 15% of the certified value for each metal. Furthermore, in those cases where the metal concentration is considered at background level, and due to the seawater matrix, Method 200.10 (US EPA 1997), on-line chelation pre-concentration and ICP-MS can then be used for quantifications, following the strict QA/QC and the appropriate use of standard reference materials such as explained hereinabove.

An inventive testing system, as exemplarily embodied, is designed to address questions about impacts of hull cleaning operations to the underwater paint systems applied on vessels and quantify the associated environmental inputs. Previous methods of addressing these questions have included measurements of paint thickness and water quality in the approximate area of operations under uncontrolled field conditions. An exemplary inventive CTTD unit simulates field conditions to the maximum extent possible in a controlled laboratory setting, allowing for control of experimental variables, paint thickness measurements in precise locations and a standardized method for evaluating existing and future cleaning device components. An inventive testing system may be embodied to accommodate emergent technologies for evaluation, such as waterjet cleaning heads, sonic cleaning heads or other hybrid systems. The inventive methodology can be implemented to perform tests on any type of materials that are painted, including current and future construction materials. An inventive testing system can also address existing emergent underwater paint technologies, including unique chemistries or components within the paint and their interaction with the natural environment.

The present invention, which is disclosed herein, is not to be limited by the embodiments described or illustrated herein, which are given by way of example and not of limitation. Other embodiments of the present invention will be apparent to those skilled in the art from a consideration of the instant disclosure, or from practice of the present invention. Various omissions, modifications, and changes to the principles disclosed herein may be made by one skilled in the art without departing from the true scope and spirit of the present invention, which is indicated by the following claims.

What is claimed is:

1. An apparatus for replicating cleaning of a structure in a liquid environment, the apparatus comprising:
   a container for a liquid;
   a cleaning device including a cleaning element for contacting a coated planar surface area of a sample, said coated planar surface area characterized by coating matter situate upon said planar surface area;
   a carrier unit that transports said sample through said liquid in said container so that said coated planar surface area contactingly moves across said cleaning element while said cleaning element is in a fixed position;
   a driver mechanism;
   wherein said contacting movement of said coated planar surface area across said cleaning element results in release of some said coating matter into said liquid in said container;
   wherein said driver mechanism includes a plurality of driver wheels;
   wherein said container includes a tank characterized by a tank length and including a plurality of trolley-wheel engagement rails along said tank length;
   wherein said carrier unit includes a trolley including a plurality of trolley wheels and a plurality of driver-wheel engagement rails;
   wherein said trolley moves in a linear direction along said tank length via engagement of said trolley wheels with said trolley-wheel engagement rails;
   wherein said driver mechanism impels said trolley via engagement of said drive wheels with said driver-wheel engagement rails.

2. The apparatus for replicating cleaning as recited in claim 1, wherein said cleaning element is characterized by a material selected from the group consisting of brush filaments, pad, sponge, carpet, and fluid.

3. The apparatus for replicating cleaning as recited in claim 1, wherein said cleaning device is characterized by rotation of said cleaning element during operation of said cleaning device in association with said coated planar surface area of said sample.

4. The apparatus for replicating cleaning as recited in claim 1, wherein said cleaning device is characterized by rotation of said cleaning element during operation of said cleaning device in association with said coated planar surface area of said sample, and wherein the apparatus further comprises:
- a linear speed sensor, that measures a speed of said trolley when impelled by said driver mechanism, said trolley moving in said linear direction along said tank length during said operation of said cleaning device in association with said coated planar surface area of said sample;
- a rotational speed sensor, that measures a speed of said rotation of said cleaning element during said operation of said cleaning device in association with said coated planar surface area of said sample;
- a torque sensor, that measures torque load characterizing said cleaning device during said operation of said cleaning device in association with said coated planar surface area of said sample;
- a computer having computer code characterized by computer program logic for evaluating said release of said coating matter into said liquid during said operation of said cleaning device in association with said coated planar surface area of said sample, said computer code being executable by said computer so that, in accordance with said computer program logic, said computer performs acts including:
  - obtaining sensory measurement values from said linear speed sensor, said rotational speed sensor, and said torque sensor during said operation of said cleaning device in association with said coated planar surface area of said sample;
  - analyzing, with respect to said coating matter, an amount of said liquid into which some said coating matter has been released during said operation of said cleaning device in association with said coated planar surface area of said sample;
  - correlating the obtained said sensory measurement values with the analyzed said amount of said liquid.

5. The apparatus for replicating cleaning as recited in claim 1, wherein:
- said tank approximately defines a rectangular prismatic shape and includes a tank bottom, two side tank walls, two end tank walls, and two said trolley-wheel engagement rails;
- said trolley-wheel engagement rails respectively extend along a portion of each said side tank wall;
- said driver mechanism includes two said driver wheels;
- said trolley approximately defines a rectangular profile and has four said trolley wheels and two said driver-wheel engagement rails;
- two said trolley wheels engage each said trolley-wheel engagement rail;
- one said driver wheel engages each said driver-wheel engagement rail.

6. The apparatus for replicating cleaning as recited in claim 5, wherein said tank bottom has a tank bottom opening, and wherein the apparatus further comprises:
- said container includes a receptacle integrated with said tank bottom at said tank bottom opening;
- the apparatus further comprises an inlet valve and an outlet valve, said inlet valve for ingress of said liquid to said tank, said outlet valve for egress of said liquid from said receptacle.

7. The apparatus for replicating cleaning as recited in claim 6, wherein:
- said tank bottom is characterized by an inclination for facilitating flow of said liquid approximate downward into said receptacle;
- said receptacle has a receptacle bottom;
- said receptacle bottom is characterized by an inclination for facilitating flow of said liquid approximately toward said outward valve.

8. The apparatus for replicating cleaning as recited in claim 7, wherein said cleaning device is characterized by rotation of said cleaning element during operation of said cleaning device in association with said coated planar surface area of said sample, and wherein the apparatus further comprises:
- a linear speed sensor, that measures a speed of said trolley when impelled by said driver mechanism, said trolley moving in said linear direction along said tank length during said operation of said cleaning device in association with said coated planar surface area of said sample;
- a rotational speed sensor, that measures a speed of said rotation of said cleaning element during said operation of said cleaning device in association with said coated planar surface area of said sample;
- a torque sensor, that measures a torque load characterizing said cleaning device during said operation of said cleaning device in association with said coated planar surface area of said sample;
- a computer having computer code characterized by computer program logic for evaluating said release of said coating matter into said liquid during said operation of said cleaning device in association with said coated planar surface area of said sample, said computer code being executable by said computer so that, in accordance with said computer program logic, said computer performs acts including:
  - obtaining sensory measurement values from said linear speed sensor, said rotational speed sensor, and said torque sensor during said operation of said cleaning device in association with said coated planar surface area of said sample;
  - analyzing, with respect to said coating matter, an amount of said liquid into which some said coating matter has been released during said operation of said cleaning device in association with said coated planar surface area of said sample;
  - correlating the obtained said sensory measurement values with the analyzed said amount of said liquid.

9. The apparatus for replicating cleaning as recited in claim 8, wherein said liquid is seawater, and wherein said cleaning element is characterized by brush filaments.

10. A method for replicating cleaning of a structure in a liquid environment, the method comprising introducing liquid into a container, coupling a sample with a carrier unit, and applying a cleaning device to said sample, said cleaning device including a cleaning element, said sample including a coated planar surface area, said coated planar surface area characterized by coating matter situate upon said planar surface area;
- wherein said applying of said cleaning device to said sample includes using said carrier unit to transport said sample through said liquid in said container so that said coated planar surface area contactingly moves across said cleaning element while said cleaning element is in a fixed position;
- wherein said contacting movement of said coated planar surface area across said cleaning element results in release of some said coating matter into said liquid in said container;

wherein said coating matter situate upon said planar surface area is characterized by a coating thickness, and wherein the method further comprises:
measuring said coating thickness prior to said applying of said cleaning device to said sample;
measuring said coating thickness subsequent to said applying of said cleaning device to said sample.

11. A method for replicating cleaning of a structure in a liquid environment, the method comprising introducing liquid into a container, coupling a sample with a carrier unit, and applying a cleaning device to said sample, said cleaning device including a cleaning element, said sample including a coated planar surface area, said coated planar surface area characterized by coating matter situate upon said planar surface area, wherein:
said applying of said cleaning device to said sample includes using said carrier unit to transport said sample through said liquid in said container so that said coated planar surface area contactingly moves across said cleaning element while said cleaning element is in a fixed position;
said contacting movement of said coated planar surface area across said cleaning element results in release of some said coating matter into said liquid in said container;
said applying of said cleaning device to said sample includes using a driver mechanism to impel said carrier unit;
said driver mechanism includes a plurality of driver wheels;
said container includes a tank characterized by a tank length and including a plurality of trolley-wheel engagement rails along said tank length;
said carrier unit includes a trolley including a plurality of trolley wheels and a plurality of driver-wheel engagement rails;
said trolley moves in a linear direction along said tank length via engagement of said trolley wheels with said trolley-wheel engagement rails;
said driver mechanism impels said trolley via engagement of said drive wheels with said driver-wheel engagement rails.

12. The method for replicating cleaning as recited in claim 11, wherein:
said tank approximately defines a rectangular prismatic shape and includes a tank bottom, two side tank walls, two end tank walls, and two said trolley-wheel engagement rails;
said trolley-wheel engagement rails respectively extend along a portion of each said side tank wall;
said driver mechanism includes two said driver wheels;
said trolley approximately defines a rectangular profile and has four said trolley wheels and two said driver-wheel engagement rails;
two said trolley wheels engage each said trolley-wheel engagement rail;
one said driver wheel engages each said driver-wheel engagement rail.

13. The method for replicating cleaning as recited in claim 12, wherein:
said introducing of said liquid into said container includes using an inlet associated with said tank;
said tank bottom has a tank bottom opening;
said container includes a receptacle integrated with said tank bottom at said tank bottom opening;
the method further comprises removing at least some said liquid from said container via said receptacle;
said removal of at least some said liquid from said container includes using an outlet associated with said receptacle.

14. The method for replicating cleaning as recited in claim 13, wherein said cleaning device is characterized by rotation of said cleaning element during operation of said cleaning device in association with said coated planar surface area of said sample, and wherein the method further comprises:
using a linear speed sensor, that measures a speed of said trolley when impelled by said driver mechanism, said trolley moving in said linear direction along said tank length during said operation of said cleaning device in association with said coated planar surface area of said sample;
using a rotational speed sensor, that measures a speed of said rotation of said cleaning element during said operation of said cleaning device in association with said coated planar surface area of said sample;
using a torque sensor, that measures a torque load characterizing said cleaning device during said operation of said cleaning device in association with said coated planar surface area of said sample;
using a computer having computer code characterized by computer program logic for evaluating said release of said coating matter into said liquid during said operation of said cleaning device in association with said coated planar surface area of said sample, said computer code being executable by said computer so that, in accordance with said computer program logic, said computer performs acts including:
obtaining sensory measurement values from said linear speed sensor, said rotational speed sensor, and said torque sensor during said operation of said cleaning device in association with said coated planar surface area of said sample;
analyzing, with respect to said coating matter, an amount of said liquid that has been removed from said container and into which some said coating matter has been released during said operation of said cleaning device in association with said coated planar surface area of said sample;
correlating the obtained said sensory measurement values with the analyzed said amount of said liquid.

15. The method for replicating cleaning as recited in claim 14, wherein said liquid is seawater, and wherein said cleaning element is characterized by brush filaments.

16. The method for replicating cleaning as recited in claim 14, wherein:
said tank approximately defines a rectangular prismatic shape and includes a tank bottom, two side tank walls, two end tank walls, and two said trolley-wheel engagement rails;
said trolley-wheel engagement rails respectively extend along a portion of each said side tank wall;
said driver mechanism includes two said driver wheels;
said trolley approximately defines a rectangular profile and has four said trolley wheels and two said driver-wheel engagement rails;
two said trolley wheels engage each said trolley-wheel engagement rail;
one said driver wheel engages each said driver-wheel engagement rail.

17. The method for replicating cleaning as recited in claim 16, wherein said coating matter situate upon said planar surface area is characterized by a coating thickness, and wherein the method further comprises:

measuring said coating thickness prior to said applying of said cleaning device to said sample;

measuring said coating thickness subsequent to said applying of said cleaning device to said sample.

\* \* \* \* \*